US00RE43098E

(19) United States
(12) Reissued Patent
Kanter et al.

(10) Patent Number: US RE43,098 E
(45) Date of Reissued Patent: Jan. 10, 2012

(54) NITROGENOUS HETEROCYCLIC COMPOUNDS AND PROCESS FOR MAKING NITROGENOUS HETEROCYCLIC COMPOUNDS AND INTERMEDIATES THEREOF

(75) Inventors: James Kanter, South San Francisco, CA (US); Anjali Pandey, Fremont, CA (US); James Robinson, Sacramento, CA (US); Robert M. Scarborough, Half Moon Bay, CA (US); Carroll Scarborough, legal representative, Half Moon Bay, CA (US)

(73) Assignee: Millennium Pharmaceuticals, Inc., Cambridge, MA (US)

(21) Appl. No.: 11/866,275

(22) Filed: Oct. 2, 2007

Related U.S. Patent Documents

Reissue of:
(64) Patent No.: 6,951,937
Issued: Oct. 4, 2005
Appl. No.: 10/041,160
Filed: Jan. 8, 2002

U.S. Applications:
(60) Provisional application No. 60/259,859, filed on Jan. 8, 2001.

(51) Int. Cl.
*A61K 31/495* (2006.01)
*C07D 487/00* (2006.01)
*C07D 487/04* (2006.01)
*C07D 239/94* (2006.01)

(52) U.S. Cl. ..... 544/284; 514/252.17

(58) Field of Classification Search ..... 514/252.17; 544/284
See application file for complete search history.

(56) References Cited

U.S. PATENT DOCUMENTS

| | | | |
|---|---|---|---|
| 3,800,039 | A | 3/1974 | Marquis |
| 4,607,034 | A | 8/1986 | Mizogami et al. |
| 4,797,419 | A | 1/1989 | Moos et al. |
| 4,983,606 | A | 1/1991 | Casagrande et al. |
| 5,120,843 | A | 6/1992 | McCall et al. |
| 5,446,062 | A | 8/1995 | Dellaria et al. |
| 5,457,105 | A | 10/1995 | Barker |
| 5,576,333 | A | 11/1996 | Miller |
| 5,591,883 | A | 1/1997 | Hwang et al. |
| 5,616,582 | A | 4/1997 | Barker |
| 5,747,498 | A | 5/1998 | Schnur |
| 5,770,599 | A | 6/1998 | Gibson |
| 5,821,246 | A | 10/1998 | Brown et al. |
| 5,962,458 | A | 10/1999 | Thomas et al. |
| 6,004,967 | A | 12/1999 | McMahon et al. |
| 6,071,921 | A | 6/2000 | Thomas et al. |
| 6,169,088 | B1 | 1/2001 | Matsuno et al. |
| 6,184,225 | B1 | 2/2001 | Thomas et al. |
| 6,207,667 | B1 | 3/2001 | Matsuno et al. |
| 6,258,951 | B1 | 7/2001 | Thomas et al. |
| 6,265,411 | B1 | 7/2001 | Thomas et al. |
| 6,291,455 | B1 | 9/2001 | Thomas et al. |
| 6,294,532 | B1 | 9/2001 | Hennequin et al. |
| 6,362,336 | B1 | 3/2002 | Thomas et al. |
| 6,414,148 | B1 | 7/2002 | Thomas et al. |
| 6,423,716 | B1 | 7/2002 | Matsuno et al. |
| 6,472,391 | B2 | 10/2002 | Matsuno et al. |
| 6,593,333 | B1 | 7/2003 | Cumming |
| 6,716,847 | B2 | 4/2004 | Cumming |
| 6,750,218 | B2 | 6/2004 | Matsuno et al. |
| 6,806,274 | B1 | 10/2004 | Crawley et al. |
| 6,897,210 | B2 | 5/2005 | Thomas et al. |
| 6,900,221 | B1 | 5/2005 | Connell et al. |
| 6,982,266 | B2 | 1/2006 | Pandey et al. |
| 7,138,413 | B1 | 11/2006 | Schwartz |
| 7,232,903 | B2 | 6/2007 | Nishino et al. |
| 7,253,164 | B2 | 8/2007 | Molteni et al. |
| 7,309,716 | B2 | 12/2007 | Wilson et al. |
| 7,329,755 | B2 | 2/2008 | Dai et al. |
| 7,368,457 | B2 | 5/2008 | Josien |
| 7,378,525 | B2 | 5/2008 | Dai et al. |
| 2002/0068734 | A1 | 6/2002 | Matsuno et al. |
| 2003/0100573 | A1 | 5/2003 | Wang et al. |
| 2003/0187053 | A1 | 10/2003 | Bertinato et al. |
| 2004/0067981 | A1 | 4/2004 | Koyama et al. |
| 2005/0070560 | A1 | 3/2005 | Himmelsbach et al. |
| 2005/0080262 | A1 | 4/2005 | Nishino et al. |

(Continued)

FOREIGN PATENT DOCUMENTS

| | | |
|---|---|---|
| EP | 0 454 498 A2 | 10/1991 |

(Continued)

OTHER PUBLICATIONS

Abstracts of the 116th Annual Meeting of the Pharmaceutical Society of Japan, Kanazawa, 2:275; 29(c2):15-21 (1996).

Agrawal, Vijai, et al. "Antiparasitic agents. Part VI: Synthesis of 7-chloro-4-(4-substituted-phenylanino)- and 7-chloro-4-(4-substituted-piperazin-1-yl) quinolines as potential antiparasitic agents" Indian J. Chem., Sect. B (1987), 26(B) 6 pp. 550-555.

Anderson, K., et al. "Oxadiazoles as bioisosteric transformations of carboxylic functionalities," Eur. J. Med. Chem 31:417-425 (1996).

Chen, S., et al. "Putative benzodiazepine partial agonists demonstrate receptor heterogeneity," Pharmacology Biochemistry and Behavior 53(1): 87-97 (1996).

Griswold, Ian, et al. "Effects of MLN518, a dual FLT3 and KIT inhibitor, on normal and malignant hematopoiesis," Blood, 2004, vol. 104, No. 9, pp. 2912-2918.

(Continued)

*Primary Examiner* — James O Wilson
*Assistant Examiner* — Tamthom N Truong
(74) *Attorney, Agent, or Firm* — Kilpatrick, Townsend & Stockton LLP

(57) ABSTRACT

The present invention provides nitrogen-containing heterocyclic compounds and pharmaceutically acceptable salts thereof and a process for making thereof. The compounds have inhibitory activity on the phosphorylation of kinases, which inhibits the activity of such kinases. The invention also provides intermediate compounds useful in the process, as well as final products produced by the process, and salts or prodrugs thereof. The invention further provides a method of inhibiting kinases and treating disease states in a mammal by inhibiting the phosphorylation of kinases comprising administering an effective amount of a compound according to the invention to a patient in need thereof.

20 Claims, No Drawings

U.S. PATENT DOCUMENTS

| | | | |
|---|---|---|---|
| 2005/0124809 | A1 | 6/2005 | Nishino et al. |
| 2005/0130995 | A1 | 6/2005 | Nishino et al. |
| 2005/0239777 | A1 | 10/2005 | Thomas et al. |
| 2006/0004017 | A1 | 1/2006 | Stokes et al. |
| 2007/0037793 | A1 | 2/2007 | Koyama et al. |
| 2007/0037795 | A1 | 2/2007 | Koyama et al. |

FOREIGN PATENT DOCUMENTS

| | | | | |
|---|---|---|---|---|
| EP | 0 535 925 | A1 | | 4/1993 |
| EP | 0 535 926 | A1 | | 4/1993 |
| EP | 0 617 001 | A1 | | 9/1994 |
| EP | 0 709 363 | A1 | | 5/1996 |
| EP | 0 790 986 | | | 5/1996 |
| EP | 0 823 419 | A2 | | 2/1998 |
| EP | 0 882 717 | A | | 12/1998 |
| EP | 0 882 717 | A1 | | 12/1998 |
| EP | 1 067 123 | A | | 1/2001 |
| EP | 1 067 123 | A1 | | 1/2001 |
| EP | 1 086 078 | B1 | | 2/2003 |
| EP | 1 466 907 | A1 | | 10/2004 |
| EP | 1 154 774 | B1 | | 6/2005 |
| EP | 1 553 097 | A1 | | 7/2005 |
| JP | S58-172379 | | | 10/1983 |
| JP | S60-120872 | | | 6/1985 |
| JP | H2-167277 | | | 6/1990 |
| JP | 5-208911 | | | 8/1993 |
| JP | 5-208911 | A | | 8/1993 |
| JP | 6-87834 | | | 3/1994 |
| JP | 06-247942 | | * | 9/1994 |
| JP | H6-247942 | A | | 9/1994 |
| JP | 11-80131 | | * | 3/1999 |
| JP | S60-120872 | | | 6/2005 |
| WO | WO 88/08424 | A1 | | 11/1988 |
| WO | WO 92/20642 | A1 | | 11/1992 |
| WO | WO 94/00444 | A1 | | 1/1994 |
| WO | WO 94/12181 | A1 | | 6/1994 |
| WO | WO 94/22834 | A1 | | 10/1994 |
| WO | WO 95/14017 | A1 | | 5/1995 |
| WO | WO 96/08486 | A1 | | 3/1996 |
| WO | WO 96/09294 | A1 | | 3/1996 |
| WO | WO 96/09818 | A1 | | 4/1996 |
| WO | WO 96/15118 | A1 | | 5/1996 |
| WO | WO 96/17833 | A1 | | 6/1996 |
| WO | WO 96/30347 | A1 | | 10/1996 |
| WO | WO 97/01569 | A1 | | 1/1997 |
| WO | WO 97/03069 | A1 | | 1/1997 |
| WO | WO 97/06802 | A1 | | 2/1997 |
| WO | WO 97/12615 | A1 | | 4/1997 |
| WO | WO 97/14685 | A1 | | 4/1997 |
| WO | WO 97/22596 | A1 | | 6/1997 |
| WO | WO 97/27748 | A1 | | 8/1997 |
| WO | WO 97/28139 | A1 | | 8/1997 |
| WO | WO 97/28141 | A1 | | 8/1997 |
| WO | WO 97/30035 | A1 | | 8/1997 |
| WO | WO 97/32856 | A1 | | 9/1997 |
| WO | WO 97/42187 | A1 | | 11/1997 |
| WO | WO 97/46562 | A1 | | 12/1997 |
| WO | WO 98/10767 | A2 | | 3/1998 |
| WO | WO 98/13354 | A1 | | 4/1998 |
| WO | WO 98/31675 | A1 | | 7/1998 |
| WO | WO 98/35959 | A1 | | 8/1998 |
| WO | WO 98/14431 | A1 | | 9/1998 |
| WO | WO 92/20642 | A1 | | 11/1998 |
| WO | WO 99/10349 | A1 | | 3/1999 |
| WO | WO 99/16751 | A1 | | 4/1999 |
| WO | WO 99/18096 | A1 | | 4/1999 |
| WO | WO 99/51582 | A1 | | 10/1999 |
| WO | WO 99/61410 | A1 | | 12/1999 |
| WO | WO 99/64394 | A1 | | 12/1999 |
| WO | WO 00/06254 | A2 | | 2/2000 |
| WO | WO 00/20402 | A1 | | 4/2000 |
| WO | WO 00/21955 | A1 | | 4/2000 |
| WO | WO 00/39118 | A1 | | 7/2000 |
| WO | WO 00/43326 | A1 | | 7/2000 |
| WO | WO 00/47212 | A1 | | 8/2000 |
| WO | WO 00/55141 | A1 | | 9/2000 |
| WO | WO 01/04102 | A1 | | 1/2001 |
| WO | WO 01/004102 | A1 | | 1/2001 |
| WO | WO 01/21594 | A1 | | 3/2001 |
| WO | WO 01/21595 | A1 | | 3/2001 |
| WO | WO 01/21596 | | | 3/2001 |
| WO | WO 01/21597 | A1 | | 3/2001 |
| WO | WO 01/34574 | A1 | | 5/2001 |
| WO | WO 01/66099 | A2 | | 9/2001 |
| WO | WO 01/77085 | A1 | | 10/2001 |
| WO | WO 01/94341 | A1 | | 12/2001 |
| WO | WO 02/00644 | A1 | | 1/2002 |
| WO | WO 02/02534 | A1 | | 1/2002 |
| WO | WO 02/16352 | A1 | | 2/2002 |
| WO | WO 02/16360 | A2 | | 2/2002 |
| WO | WO 02/16361 | A2 | | 2/2002 |
| WO | WO 02/16362 | A2 | | 2/2002 |
| WO | WO 02/18372 | A1 | | 3/2002 |
| WO | WO 02/30924 | | | 4/2002 |
| WO | WO 02/30926 | | | 4/2002 |
| WO | WO 02/34744 | | | 5/2002 |
| WO | WO 02/36587 | | | 5/2002 |
| WO | WO 02/059074 | A1 | | 8/2002 |
| WO | WO 02/070509 | A2 | | 9/2002 |
| WO | WO 02/072578 | A2 | | 9/2002 |
| WO | WO 02/085895 | A1 | | 10/2002 |
| WO | WO 02/087587 | | | 11/2002 |
| WO | WO 02/092577 | | | 11/2002 |
| WO | WO 02/092578 | | | 11/2002 |
| WO | WO 02/092579 | A1 | | 11/2002 |
| WO | WO 03/045364 | | | 6/2003 |
| WO | WO 03/045943 | | | 6/2003 |
| WO | WO 03/054819 | | | 7/2003 |
| WO | WO 03/055491 | | | 7/2003 |
| WO | WO 03/064399 | | | 8/2003 |
| WO | WO 03/066602 | A1 | | 8/2003 |
| WO | WO 2004/026829 | A2 | | 4/2004 |
| WO | WO 2004/33441 | | | 4/2004 |
| WO | WO 2004/033463 | | | 4/2004 |
| WO | WO 2004/056809 | A1 | | 7/2004 |
| WO | WO 2004/089918 | A1 | | 10/2004 |
| WO | WO 2004/085418 | A3 | | 1/2005 |
| ZA | 6706512 | | | 10/1967 |

OTHER PUBLICATIONS

Kelly, Louise, et al. "CT53518, a novel selective FLT3 antagonist for the treatment of acute myelogenous leukemia (AML)," Cancer Cell, 2002, vol. 1, pp. 421-432.

Kovalenko, M., et al. "Selective platelet-derived growth factor receptor kinase blockers reverse sis-transformation," Cancer Research 54:6106-6114 (1994).

LeMahieu, Ra, et al., "(E)-3-(4-Oxo-4H-quinazolin-3-yl)-2-propenoic acids, a new series of antiallergy agents." J. Med. Chem., 1983, vol. 26, No. 3, pp. 420-425.

Matsuno et al., "Potent and Selective Inhibitors of Platelet-Derived Growth Factor Receptor Phosphorylation. 1. Synthesis, Structure-Activity Relationship, and Biological Effects of a New Class of Quinazoline Derivatives." Journal of Medicinal Chemistry, vol. 45, No. 14, pp. 3057-3066, 2002.

Pandey, Anjali, et al. "Identification of Orally Active, Potent and Selective 4-Piperazinylquinazolines as Antagonists of the Platelet-Derived Growth Factor Receptor Tyrosine Kinase Family," J. Med. Chem., 2002, vol. 45, pp. 3772-3793.

Patent Abstracts of Japan vol. 8, No. 3, Jan. 7, 1984 & JP 58 172379 A (Showa Denko KK), Oct. 11, 1983 (Abstract).

Patent Abstracts of Japan vol. 18, No. 639, Dec. 6, 1994 & JP 06 247942 A (Kyowa Hakko Kogyo Co. Ltd.), Sep. 6, 1994 (Abstract).

Patent Abstracts of Japan vol. 9, No. 271, Oct. 29, 1985 & JP 60 120872 A (Kyowa Hakko Kogyo Co., Ltd.) Jun. 28, 1985 (Abstract).

Robinson et al., "Novel inhibitors of procollagen C-Proteinase. Part 2: glutamic acid hydroxamates." Bioorganic & Medicinal Chemistry Letters, vol. 13, No. 14, pp. 2381-2381, 2003.

Agrawal, V. et al., "Antiparasitic agents: Part VI—synthesis of 7-chloro-4-(4-substituted-phenylamino)- & 7-chloro-4-(4-substituted-piperazin-1-yl)quinolines as potential antiparasitic agents" Indian Journal of Chemistry 26B:550-555 (1987).

* cited by examiner

NITROGENOUS HETEROCYCLIC COMPOUNDS AND PROCESS FOR MAKING NITROGENOUS HETEROCYCLIC COMPOUNDS AND INTERMEDIATES THEREOF

Matter enclosed in heavy brackets [ ] appears in the original patent but forms no part of this reissue specification; matter printed in italics indicates the additions made by reissue.

RELATED APPLICATIONS

This application *is a reissue application of U.S. patent application Ser. No. 10/041,160, filed Jan. 8, 2002, now U.S. Pat. No. 6,951,937 and* claims the benefit of priority under 35 U.S.C. 119(e) to [U.S. Provisional Application No. 60/244,655 filed on Nov. 1, 2000 and] U.S. Provisional Application No. 60/259,859 filed on Jan. 8, 2001 which [are] *is* herein incorporated in their entirety by reference.

FIELD OF INVENTION

The present invention relates to nitrogen-containing heterocyclic compounds and pharmaceutically acceptable salts or prodrugs thereof which have inhibitory activity on the phosphorylation of kinases, which inhibits the activity of such kinases. The invention also relates to a process for making nitrogen-containing heterocyclic compounds and intermediate compounds thereof, and pharmaceutically acceptable salts or prodrugs thereof. The invention further relates to a method of using the compounds of the present invention by inhibiting kinases and treating disease states in a mammal by inhibiting the phosphorylation of kinases by administering an effective amount of a compound according to the invention to a patient in need thereof.

BACKGROUND OF THE INVENTION

Platelet derived growth factor (PDGF) is known to act as an aggravating factor for cell-proliferative diseases such as arteriosclerosis, vascular reobstruction after percutaneous coronary angioplasty and bypass operation, cancer, glomerulonephritis, glomerulosclerosis, psoriasis and articular rheumatism. See Cell, 46: 155-169 (1986); Science, 253: 1129-1132 (1991); Nippon Rinsho (Japanese J. of Clinical Medicine), 50: 3038-3045 (1992); Nephrol Dial Transplant, 10: 787-795 (1995); Kidney International, 43 (Suppl. 39): 86-89 (1993); Journal of Rheumatology, 21: 1507-1511 (1994); Scandinavian Journal of Immunology, 27: 285-294 (1988).

Quinazoline derivatives which are useful as drugs, N,N-dimethyl-4-(6,7-dimethoxy-4-quinazolinyl)-1-piperazine carboxamide is described as a bronchodilator in South African Patent No. 67 06512 (1968). Dimethoxyquinazoline derivatives are described as inhibitors of phosphorylation of epidermal growth factor (EGF) receptor in Japanese Published Unexamined Patent Application No. 208911/93 and WO 96/09294. Quinoline derivatives having benzodiazepin receptor agonist activity are described in Pharmacology Biochemistry and Behavior, 53, 87-97 (1996) and European Journal of Medicinal Chemistry, 31, 417-425 (1996), and quinoline derivatives which are useful as anti-parasite agents are described in Indian Journal of Chemistry, 26B: 550-555 (1987).

Inhibitors of phosphorylation of PDGF receptor so far known include bismono- and bicyclic aryl compounds and heteroaryl compounds (WO 92/20642), quinoxaline derivatives. See Cancer Research, 54: 6106 (1994), pyrimidine derivatives (Japanese Published Unexamined Patent Application No. 87834/94) and dimethoxyquinoline derivatives Abstracts of the 16th Annual Meeting of the Pharmaceutical Society of Japan (Kanazawa) (1996), 2: 275; 29(C2): 15-21. Nitrogenous heterocyclic compounds are also described in WO 98/14431 published on Apr. 9, 1998. The WO document describes various processes for making such compounds and phosphorylation inhibition activity thereof.

SUMMARY OF THE INVENTION

The present invention is directed to nitrogen-containing heterocyclic compounds and pharmaceutically acceptable salts thereof. These compounds have inhibitory activity on the phosphorylation of kinases, which inhibits the activity of the kinases. More particularly, important kinase inhibition according to the present invention is of receptor tyrosine kinases including platelet-derived growth factor (PDGF) receptor, Flt3, CSF-1R, epidermal growth factor receptor (EGRF), fibroblast growth factor (FGF), vascular endothelial growth factor receptor (VEGFR) and others. Another class of kinase inhibition according to the invention is inhibitory activity nonreceptor tyrosine kinases including src and abl, and the like. A third class of kinase inhibition according to the invention is inhibitory activity toward serine/threonine kinases, including such kinases as MAPK, MEK and cyclin dependent kinases (CDKs) that mediate cell proliferation, AKT and CDK such that mediate cell survival and NIK that regulate inflammatory responses. Inhibition of such kinases can be used to treat diseases involving cell survival, proliferation and migration, including cardiovascular disease, such as arteriosclerosis and vascular reobstruction, cancer, glomerulosclerosis fibrotic diseases and inflammation, as well as the general treatment of cell-proliferative diseases.

One aspect of the present invention relates to a process for making nitrogen-containing heterocyclic compounds represented by formula A as follows:

A

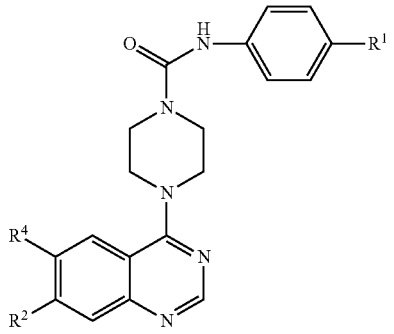

wherein $R^1$ is a member selected from the group consisting of:

—CN, —O—$C_{1-8}$ alkyl that is straight or branched chained, —O-phenyl, —O-naphthyl, —O-indolyl and —O-isoquinolinyl;

$R^2$ and $R^4$ are each independently a member selected from the group consisting of:

hydrogen, —O—$CH_3$, —O(—$CH_2$)—$CH_3$, —O(—$CH_2$)$_2$—$CH_3$, —O—$CH_2$—CH═$CH_2$, —O—$CH_2$—C≡CH and —O(—$CH_2$)$_n$—$R^3$; wherein one of the $R^2$ and $R^4$ groups is —O(—$CH_2$)$_n$—$R^3$ and the remaining $R^2$ or $R^4$ group is other than —O(—$CH_2$)$_n$—$R^3$;

n is 2 to 5;

$R^3$ is a member selected from the group consisting of:

—OH, —O—$CH_3$, —O—$CH_2$—$CH_3$, —$NH_2$, —N(—$CH_3$)$_2$, —NH(—$CH_2$-phenyl), —NH(-phenyl), —CN

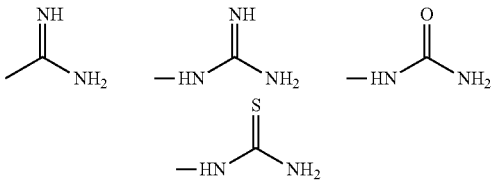

and a 4 to 10 member mono or bicyclic saturated, partially unsaturated or fully unsaturated heterocyclic ring system having at least 1 nitrogen atom and from 0 to 3 additional hetero atoms selected from the group consisting of O, N, and S, wherein the ring system may be unsubstituted or may be substituted by 1 to 4 members selected from the group consisting of H, halo, halo loweralkyl, lower alkyl, lower alkynyl, lower acyl, lower alkoxy, hydroxy, nitro, amino and the like, wherein the ring system may be attached directly to the neighboring methylene group or may be attached via an ether bond, and all pharmaceutically acceptable isomers, salts, hydrates, solvates and prodrug derivatives thereof.

Another aspect of the invention relates to a process for the production of such compounds wherein $R^3$ is a member selected from the group consisting of:

—OH, —O—$CH_3$, —O—$CH_2$—$CH_3$, —$NH_2$, —N(—$CH_3$)$_2$, —NH(—$CH_2$-phenyl), —NH(-Phenyl), —CN

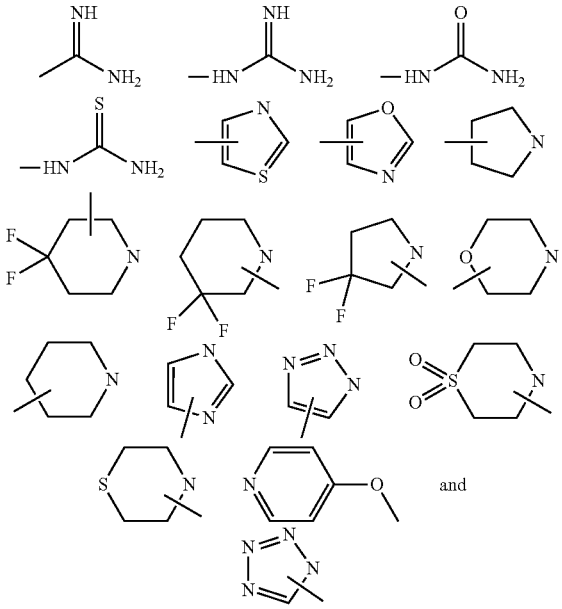

and all pharmaceutically acceptable isomers, salts, hydrates, solvates and prodrug derivatives thereof.

Another aspect of the invention relates to a process for making compounds according to formula A above of such compounds wherein $R^1$ is a member selected from the group consisting of CN, —O-methyl, —O-ethyl, —O-propyl, —O-isopropyl, —O-butyl, —O-t-butyl, —O-isoamyl, 1-naphthyloxy, 2-naphthyloxy, 4-indolyloxy, 5-indolyloxy, 5-isoquinolyloxy, and position isomers and homologs thereof, and all pharmaceutically acceptable isomers, salts, hydrates, solvates and prodrug derivatives of such compounds.

Still another aspect of the invention relates to a process for making pharmaceutically acceptable salts of the compounds according to formula (A) which include pharmaceutically acceptable acid addition salts, metal salts, ammonium salts, organic amine addition salts, amino acid addition salts, and the like.

Another aspect of invention relates to a process for making compounds according to formula A(1) and formula A(2) as follows:

Formula A(1)

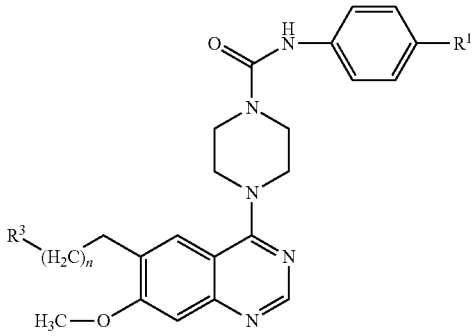

Formula A(2)

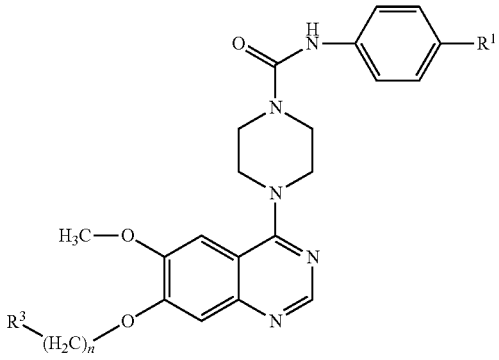

wherein $R^1$ is a member selected from the group consisting of:

—CN, —O—$C_{1-8}$ alkyl that is straight or branched chained, —O-phenyl, —O-naphthyl, —O-indolyl and —O-isoquinolinyl;

and all pharmaceutically acceptable isomers, salts, hydrates, solvates and prodrug derivatives thereof.

Another aspect of the invention relates to a process for making compounds according to formula A(1) or A(2) above wherein $R^1$ is —O-isopropyl or CN, n is 2 or 3, and $R^3$ is a cyclic amine, as well as position isomers and homologues thereof, and all pharmaceutically acceptable isomers, salts, hydrates, solvates and prodrug derivatives of such compounds.

Still another aspect of the invention relates to a process for preparing compounds according to formula A(1) or A(2)

wherein n is 3, $R^1$ is —O-isopropyl or CN and $R^3$ is a member selected from the group consisting of:

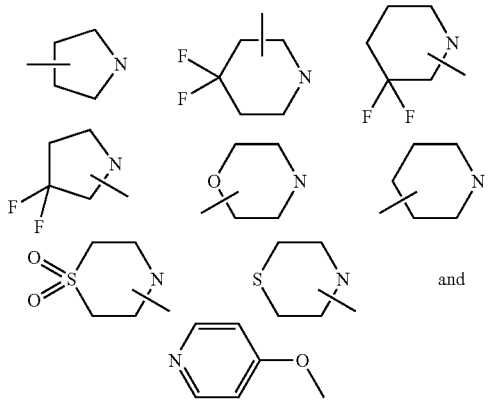

and all pharmaceutically acceptable isomers, salts, hydrates, solvates and prodrug derivatives thereof.

Another aspect of the invention relates to a process for preparing compounds according to formula A(1) or A(2) wherein n is 3, $R^1$ is —O-isopropyl or CN and $R^3$ is a 4-6 membered saturated cyclic amine selected from the group consisting of:

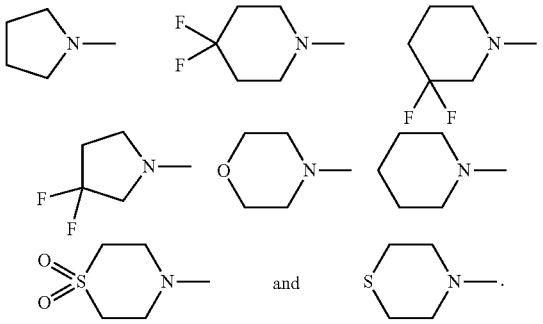

and all pharmaceutically acceptable isomers, salts, hydrates, solvates and prodrug derivatives thereof.

Another aspect of the present invention relates to a process for making compounds and pharmaceutically acceptable salts thereof which inhibit or prevent inhibition of phosphorylation of at least one PDGF receptor by at least one tyrosine kinase. Such PDGF receptor kinase inhibition can hinder abnormal cell growth and cell wandering, and thus such compounds are useful for the prevention or treatment of cell-proliferative diseases such as arteriosclerosis, vascular reobstruction, cancer and glomerulosclerosis.

Other aspects, objects, features and advantages of the present invention would be apparent to one of ordinary skill in the art from the following detailed description illustrating the preferred embodiments of the invention.

DETAILED DESCRIPTION OF THE INVENTION

Definitions

In accordance with the present invention and as used herein, the following terms are defined with the following meanings, unless explicitly stated otherwise.

The term "alkenyl" refers to a trivalent straight chain or branched chain unsaturated aliphatic radical. The term "alkinyl" (or "alkynyl") refers to a straight or branched chain aliphatic radical that includes at least two carbons joined by a triple bond. If no number of carbons is specified alkenyl and alkinyl each refer to radicals having from 2-12 carbon atoms.

The term "alkyl" refers to saturated aliphatic groups including straight-chain, branched-chain and cyclic groups having the number of carbon atoms specified, or if no number is specified, having up to 12 carbon atoms. The term "cycloalkyl" as used herein refers to a mono-, bi-, or tricyclic aliphatic ring having 3 to 14 carbon atoms and preferably 3 to 7 carbon atoms.

As used herein, the terms "carbocyclic ring structure" and "$C_{3-16}$ carbocyclic mono, bicyclic or tricyclic ring structure" or the like are each intended to mean stable ring structures having only carbon atoms as ring atoms wherein the ring structure is a substituted or unsubstituted member selected from the group consisting of: a stable monocyclic ring which is aromatic ring ("aryl") having six ring atoms; a stable monocyclic non-aromatic ring having from 3 to 7 ring atoms in the ring; a stable bicyclic ring structure having a total of from 7 to 12 ring atoms in the two rings wherein the bicyclic ring structure is selected from the group consisting of ring structures in which both of the rings are aromatic, ring structures in which one of the rings is aromatic and ring structures in which both of the rings are non-aromatic; and a stable tricyclic ring structure having a total of from 10 to 16 atoms in the three rings wherein the tricyclic ring structure is selected from the group consisting of: ring structures in which three of the rings are aromatic, ring structures in which two of the rings are aromatic and ring structures in which three of the rings are non-aromatic. In each case, the non-aromatic rings when present in the monocyclic, bicyclic or tricyclic ring structure may independently be saturated, partially saturated or fully saturated. Examples of such carbocyclic ring structures include, but are not limited to, cyclopropyl, cyclobutyl, cyclopentyl, cyclohexyl, adamantyl, cyclooctyl, [3.3.0]bicyclooctane, [4.3.0]bicyclononane, [4.4.0]bicyclodecane (decalin), 2.2.2] bicyclooctane, fluorenyl, phenyl, naphthyl, indanyl, adamantyl, or tetrahydronaphthyl (tetralin). Moreover, the ring structures described herein may be attached to one or more indicated pendant groups via any carbon atom which results in a stable structure. The term "substituted" as used in conjunction with carbocyclic ring structures means that hydrogen atoms attached to the ring carbon atoms of ring structures described herein may be substituted by one or more of the substituents indicated for that structure if such substitution(s) would result in a stable compound.

The term "aryl" which is included with the term "carbocyclic ring structure" refers to an unsubstituted or substituted aromatic ring, substituted with one, two or three substituents selected from loweralkoxy, loweralkyl, loweralkylamino, hydroxy, halogen, cyano, hydroxyl, mercapto, nitro, thioalkoxy, carboxaldehyde, carboxyl, carboalkoxy and carboxamide, including but not limited to carbocyclic aryl, heterocyclic aryl, and biaryl groups and the like, all of which may be optionally substituted. Preferred aryl groups include phenyl, halophenyl, loweralkylphenyl, naphthyl, biphenyl, phenanthrenyl and naphthacenyl.

The term "arylalkyl" which is included with the term "carbocyclic aryl" refers to one, two, or three aryl groups having the number of carbon atoms designated, appended to an alkyl group having the number of carbon atoms designated. Suitable arylalkyl groups include, but are not limited to, benzyl, picolyl, naphthylmethyl, phenethyl, benzyhydryl, trityl, and the like, all of which may be optionally substituted.

As used herein, the term "heterocyclic ring" or "heterocyclic ring system" is intended to mean a substituted or unsubstituted member selected from the group consisting of stable monocyclic ring having from 5-7 members in the ring itself and having from 1 to 4 hetero ring atoms selected from the group consisting of N, O and S; a stable bicyclic ring structure having a total of from 7 to 12 atoms in the two rings wherein at least one of the two rings has from 1 to 4 hetero atoms selected from N, O and S, including bicyclic ring structures wherein any of the described stable monocyclic heterocyclic rings is fused to a hexane or benzene ring; and a stable tricyclic heterocyclic ring structure having a total of from 10 to 16 atoms in the three rings wherein at least one of the three rings has from 1 to 4 hetero atoms selected from the group consisting of N, O and S. Any nitrogen and sulfur atoms present in a heterocyclic ring of such a heterocyclic ring structure may be oxidized. Unless indicated otherwise, the terms "heterocyclic ring" or "heterocyclic ring system" include aromatic rings, as well as non-aromatic rings which can be saturated, partially saturated or fully saturated non-aromatic rings. Also, unless indicated otherwise the term "heterocyclic ring system" includes ring structures wherein all of the rings contain at least one hetero atom as well as structures having less than all of the rings in the ring structure containing at least one hetero atom, for example bicyclic ring structures wherein one ring is a benzene ring and one of the rings has one or more hetero atoms are included within the term "heterocyclic ring systems" as well as bicyclic ring structures wherein each of the two rings has at least one hetero atom. Moreover, the ring structures described herein may be attached to one or more indicated pendant groups via any hetero atom or carbon atom which results in a stable structure. Further, the term "substituted" means that one or more of the hydrogen atoms on the ring carbon atom(s) or nitrogen atom(s) of the each of the rings in the ring structures described herein may be replaced by one or more of the indicated substituents if such replacement (s) would result in a stable compound. Nitrogen atoms in a ring structure may be quaternized, but such compounds are specifically indicated or are included within the term "a pharmaceutically acceptable salt" for a particular compound. When the total number of O and S atoms in a single heterocyclic ring is greater than 1, it is preferred that such atoms not be adjacent to one another. Preferably, there are no more that 1 O or S ring atoms in the same ring of a given heterocyclic ring structure.

Examples of monocyclic and bicyclic heterocyclic ring systems, in alphabetical order, are acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalinyl, carbazolyl, 4aH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pryidooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl. Preferred heterocyclic ring structures include, but are not limited to, pyridinyl, furanyl, thienyl, pyrrolyl, pyrazolyl, pyrrolidinyl, imidazolyl, indolyl, benzimidazolyl, 1H-indazolyl, oxazolinyl, or isatinoyl. Also included are fused ring and spiro compounds containing, for example, the above heterocyclic ring structures.

As used herein the term "aromatic heterocyclic ring system" has essentially the same definition as for the monocyclic and bicyclic ring systems except that at least one ring of the ring system is an aromatic heterocyclic ring or the bicyclic ring has an aromatic or non-aromatic heterocyclic ring fused to an aromatic carbocyclic ring structure.

The terms "halo" or "halogen" as used herein refer to Cl, Br, F or I substituents. The term "haloalkyl", and the like, refer to an aliphatic carbon radicals having at least one hydrogen atom replaced by a Cl, Br, F or I atom, including mixtures of different halo atoms. Trihaloalkyl includes trifluoromethyl and the like as preferred radicals, for example.

The term "methylene" refers to —$CH_2$—.

The term "leaving group" in the definition of $L_1$, $L_2$ and Q include halogen atoms, substituted or unsubstituted alkoxy groups, substituted or unsubstituted aryloxy groups, substituted or unsubstituted alkylthio groups, substituted or unsubstituted alkylsulfinyl groups, substituted or unsubstituted alkylsulfonyl groups, substituted or unsubstituted alkylsulfonyloxy groups, substituted or unsubstituted arylsulfonyloxy groups, and the like. The halogen atom, alkoxy group, aryloxy group, alkylthio group and alkylsulfinyl group have the same meanings as defined above, respectively, the alkyl moiety of the alkylsulfonyl group and alkylsulfonyloxy group has the same meaning as the alkyl group defined above, and the aryl moiety of the arylsulfonyloxy group has the same meaning as the aryl defined above. Examples of the substituent include halogen atoms, alkyl groups, a nitro group, and the like, and the halogen atom has the same meaning as the halogen atom defined above. Other examples include methane sulfonate and p-toluene sulfonate.

The term "pharmaceutically acceptable salts" include salts of compounds derived from the combination of a compound and an organic or inorganic acid. These compounds are useful in both free base and salt form. In practice, the use of the salt form amounts to use of the base form; both acid and base addition salts are within the scope of the present invention.

"Pharmaceutically acceptable acid addition salt" refers to salts retaining the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly preferred organic nontoxic bases are isopropylamine, diethylamine, ethanolamine, trimethamine, dicyclohexylamine, choline, and caffeine.

This invention also encompasses prodrug derivatives of the compounds contained herein. The term "prodrug" refers to a pharmacologically inactive derivative of a parent drug molecule that requires biotransformation, either spontaneous or enzymatic, within the organism to release the active drug. Prodrugs are variations or derivatives of the compounds of this invention which have groups cleavable under metabolic conditions. Prodrugs become the compounds of the invention which are pharmaceutically active in vivo, when they undergo solvolysis under physiological conditions or undergo enzymatic degradation. Prodrug compounds of this invention may be called single, double, triple etc., depending on the number of biotransformation steps required to release the active drug within the organism, and indicating the number of functionalities present in a precursor-type form. Prodrug forms often offer advantages of solubility, tissue compatibility, or delayed release in the mammalian organism (see, Bundgard, Design of Prodrugs, pp. 7-9, 21-24, Elsevier, Amsterdam 1985 and Silverman, The Organic Chemistry of Drug Design and Drug Action, pp. 352-401, Academic Press, San Diego, Calif., 1992). Prodrugs commonly known in the art include acid derivatives well known to practitioners of the art, such as, for example, esters prepared by reaction of the parent acids with a suitable alcohol, or amides prepared by reaction of the parent acid compound with an amine, or basic groups reacted to form an acylated base derivative. Moreover, the prodrug derivatives of this invention may be combined with other features herein taught to enhance bioavailability.

"Biological property" for the purposes herein means an in vivo effect or antigenic function or activity that is directly or indirectly performed by a compound of this invention that are often shown by in vitro assays. Effector functions include receptor or ligand binding, any enzyme activity or enzyme modulatory activity, any carrier binding activity, any hormonal activity, any activity in promoting or inhibiting adhesion of cells to an extracellular matrix or cell surface molecules, or any structural role. Antigenic functions include possession of an epitope or antigenic site that is capable of reacting with antibodies raised against it.

The present invention relates to a process for making nitrogen-containing heterocyclic compounds represented by formula A as follows:

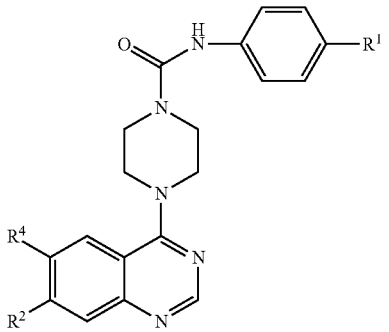

wherein $R^1$ is a member selected from the group consisting of:

—CN, —O—$C_{1-8}$ alkyl that is straight or branched chained, —O-phenyl, —O-naphthyl, —O-indolyl and —O-isoquinolinyl;

$R^2$ and $R^4$ are each independently a member selected from the group consisting of:

hydrogen, —O—$CH_3$, —O(—$CH_2$)—$CH_3$, —O(—$CH_2$)$_2$—$CH_3$, —O—$CH_2$—CH═$CH_2$, —O—$CH_2$—C≡CH and —O(—$CH_2$)$_n$—$R^3$; wherein one of the $R^2$ and $R^4$ groups is —O(—$CH_2$)$_n$—$R^3$ and the remaining $R^2$ or $R^4$ group is other than —O(—$CH_2$)$_n$—$R^3$;

n is 2 to 5;

$R^3$ is a member selected from the group consisting of:

—OH, —O—$CH_3$, —O—$CH_2$—$CH_3$, —$NH_2$, —N(—$CH_3$)$_2$, —NH(—$CH_2$-phenyl), —NH(-phenyl), —CN

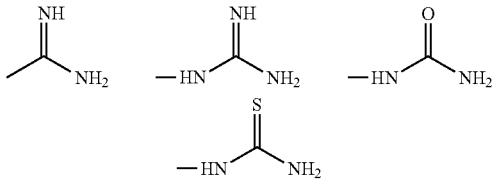

and a 4 to 10 member mono or bicyclic saturated, partially unsaturated or fully unsaturated heterocyclic ring system having at least 1 nitrogen atom and from 0 to 3 additional hetero atoms selected from the group consisting of O, N, and S, wherein the ring system may be unsubstituted or may be substituted by 1 to 4 members selected from the group consisting of H, halo, halo loweralkyl, lower alkyl, lower alkynyl, lower acyl, lower alkoxy, hydroxy, nitro, amino and the like, wherein the ring system may be attached directly to the neighboring methylene group or may be attached via an ether bond, and all pharmaceutically acceptable isomers, salts, hydrates, solvates and prodrug derivatives thereof.

A preferred process is a process for the production of such compounds wherein $R^3$ is a member selected from the group consisting of:

—OH, —O—$CH_3$, —O—$CH_2$—$CH_3$, —$NH_2$, —N(—$CH_3$)$_2$, —NH(—$CH_2$-phenyl), —NH(-Phenyl), —CN

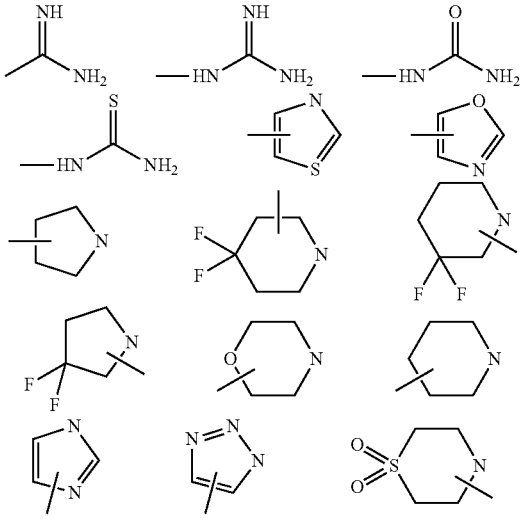

-continued

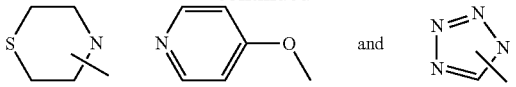

and all pharmaceutically acceptable isomers, salts, hydrates, solvates and prodrug derivatives thereof.

A particularly preferred process is a process for making compounds according to formula A above wherein $R^1$ is a member selected from the group consisting of CN, —O-methyl, —O-ethyl, —O-propyl, —O-isopropyl, —O-butyl, —O-t-butyl, —O-isoamyl, 1-naphthyloxy, 2-naphthyloxy, 4-indolyloxy, 5-indolyloxy, 5-isoquinolyloxy, and position isomers and homologs thereof, and all pharmaceutically acceptable isomers, salts, hydrates, solvates and prodrug derivatives of such compounds. More preferred is a process for making compounds wherein n is 2 or 3 and $R^1$ is —O-isopropyl or CN and $R^3$ is a cyclic amine.

The process also provides for making pharmaceutically acceptable salts of the compounds according to formula (A) which include pharmaceutically acceptable acid addition salts, metal salts, ammonium salts, organic amine addition salts, amino acid addition salts, etc. Examples of the pharmaceutically acceptable acid addition salts of the compounds of formula (A) are inorganic acid addition salts such as hydrochloride, sulfate and phosphate, and organic acid addition salts such as acetate, maleate, fumarate, tartrate, citrate and methanesulfonate. Examples of the pharmaceutically acceptable metal salts are alkali metal salts such as sodium salt and potassium salt, alkaline earth metal salts such as magnesium salt and calcium salt, aluminum salt and zinc salt. Examples of the pharmaceutically acceptable ammonium salts are ammonium salt and tetramethyl ammonium salt. Examples of the pharmaceutically acceptable organic amine addition salts include heterocyclic amine salts such as morpholine and piperidine salts. Examples of the pharmaceutically acceptable amino acid addition salts are salts with lysine, glycine and phenylalanine. The process also provides for making pharmaceutically acceptable isomers, hydrates, solvates and prodrug derivatives of the compounds according to formula (A) and would be apparent to one of ordinary skill in the art.

The present process invention can be readily adapted to make other compounds in the art, such as the nitrogenous heterocyclic compounds described in WO 98/14431 published on Apr. 9, 1998. Accordingly, the present invention also provides for making such compounds using the present procedures or readily apparent variations thereon.

In a preferred embodiment the invention provides a process for making compounds according to formula A(1) and formula A(2) as follows:

Formula A(1)

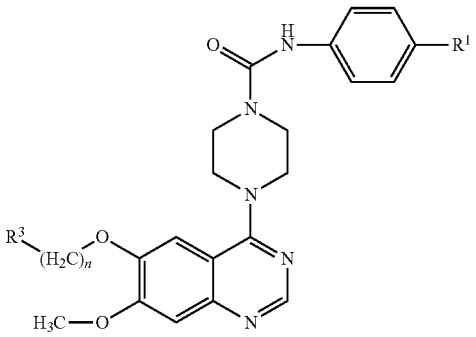

-continued

Formula A(2)

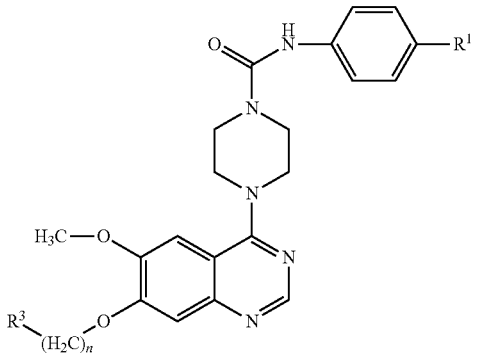

wherein $R^1$ is a member selected from the group consisting of:

—CN, —O—$C_{1-8}$ alkyl that is straight or branched chained, —O-phenyl, —O-naphthyl, —O-indolyl and —O-isoquinolinyl;

and all pharmaceutically acceptable isomers, salts, hydrates, solvates and prodrug derivatives thereof.

A particularly preferred process is a process for making compounds according to formula A(1) or A(2) above wherein $R^1$ is —O-isopropyl or CN, n is 2 or 3, and $R^3$ is a cyclic amine, as well as position isomers and homologues thereof, and all pharmaceutically acceptable isomers, salts, hydrates, solvates and prodrug derivatives of such compounds.

A more preferred is a process for making compounds according to formula A(1) or A(2) wherein n is 3, $R^1$ is —O-isopropyl or CN and $R^3$ is a member selected from the group consisting of:

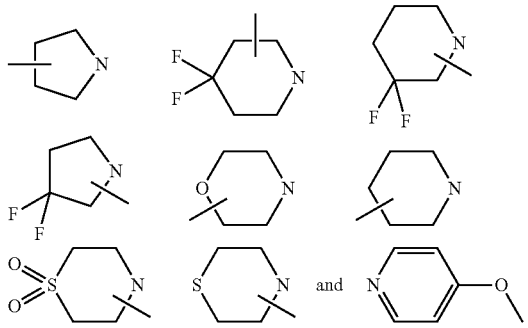

and all pharmaceutically acceptable isomers, salts, hydrates, solvates and prodrug derivatives thereof.

Further preferred is such a process wherein n is 3, $R^1$ is —O-isopropyl or CN and $R^3$ is a 4-6 membered saturated cyclic amine selected from the group consisting of:

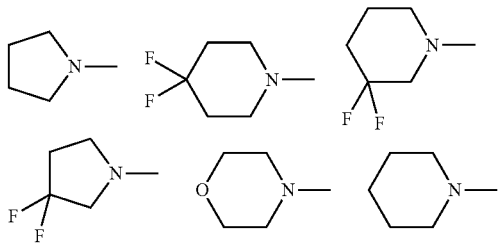

-continued

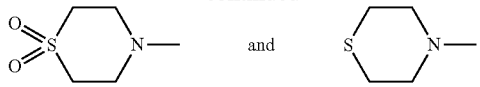

and all pharmaceutically acceptable isomers, salts, hydrates, solvates and prodrug derivatives thereof.

Most preferable is a process for making such compounds of formula A(1) or A(2) wherein n is 3, $R^1$ is —O-isopropyl or CN and $R^3$ is N-piperidine or N-pyrrolidine.

The pharmaceutically acceptable salts of the compounds according to formula (A) include pharmaceutically acceptable acid addition salts, metal salts, ammonium salts, organic amine addition salts, amino acid addition salts, etc.

The present invention process is not limited by the above listed compounds, but includes intermediates for making such compounds or other related compounds. Analogs of the bicyclic compounds are contemplated and would be apparent to one of ordinary skill in the art.

The compounds may be prepared using methods and procedures generally as described below, however other leaving groups may be utilized.

The present invention is directed to a process for preparing nitrogen-containing heterocyclic compound of formula A and pharmaceutically acceptable salts thereof,

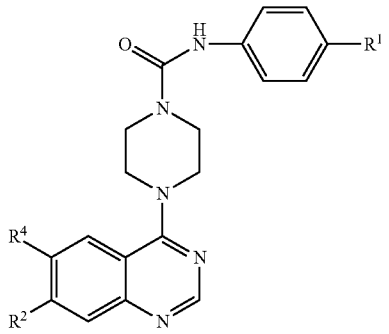

A comprising the steps of:

(a) etherifying the hydroxy group of a compound of formula I or its position isomer with a compound of formula II wherein $L_1$ is a leaving group such as Cl and the like, which is less reactive than an ether forming leaving group $L_2$ such as Br and the like, *or when n is 1, $L_1$ may also be —H, —CH═CH$_2$ or —C≡CH, or when n is 0 or 2, $L_1$ may also be —H;* under basic etherification conditions, preferably wherein the base is preferably potassium carbonate, sodium carbonate, sodium hydroxide and the like, in the presence of an appropriate solvent such as toluene, methanol, ethanol, ether, THF and the like, preferably ethanol or toluene, at reflux temperature of the solvent about 2-6 hours, preferably about 3 to 4 hours to produce a compound of formula III or its position isomer as follows:

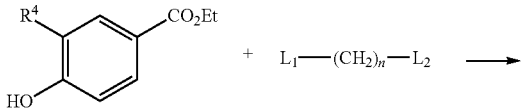

I II

-continued

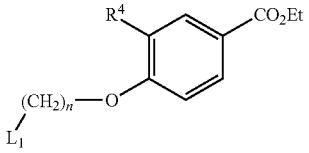

III (b) nitrating a compound according to formula III, or its position isomer, to yield a compound according to formula IV, or its position isomer, preferably at a temperature of from about 0° C. to 80° C., preferably about 0° C. to 20° C. in nitric acid and an appropriate solvent such as a mixture of acetic acid and dichloromethane, as follows:

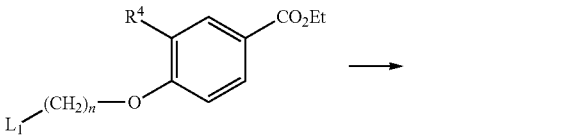

III

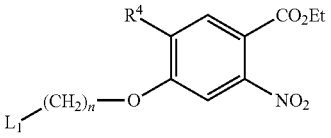

IV

*and when $L_1$ is a leaving group further comprising* (c) reacting the compound of formula IV, or its position isomer, with an amine containing compound for the appropriate $R^3$ group, such as a piperidine, pyrrolidine, morpholine, piperazine, 4-methyl piperidine or 2-methyl-piperidine, in the presence of a basic catalyst such as potassium carbonate, sodium carbonate, sodium hydroxide, and the like, preferably potassium carbonate and sodium iodine and a solvent such as toluene, ethanol, THF, ether, glyme, diglyme, MTBE, or the like, to replace the $L_1$ group with an $R^3$ group, and provide a compound of formula V, or its position isomer, as follows:

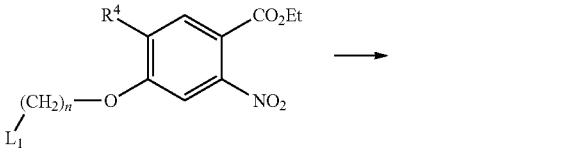

IV

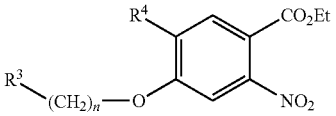

V (d) reducing the nitro group on the compound of formula V, or on its position isomer, to an amino group and thereby producing a compound of formula VI, or its position isomer, as follows:

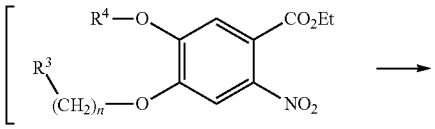

V

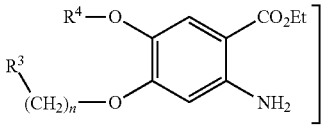

VI

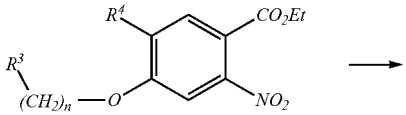

*V*

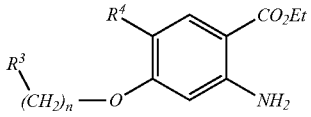

*VI*

(e) reacting the compound or formula V*I*, or its position isomer with ammonium formate and formamide at about 120° C. to 140° C., preferably, at about 130° C. to produce a cyclized quinazoline derivative of formula VII, or its position isomer, as follows:

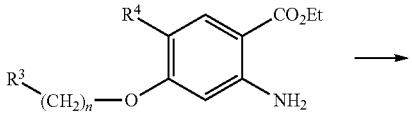

VI

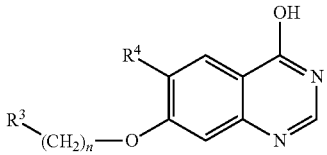

VII f) replacing the hydroxy group of the compound of formula VII, or its position isomer, with a leaving group Q, preferably Q is the leaving groups bromo, chloro, p-toluene sulfonate, methyl sulfonate and the like, preferably chloro which is derived from a chlorinating agent such as thionyl chloride, to provide a compound of formula VIII, or its position isomer, as follows:

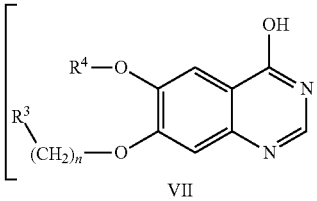

VII

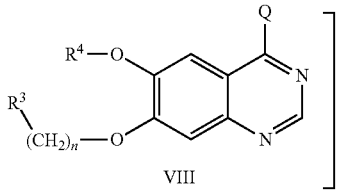

VIII

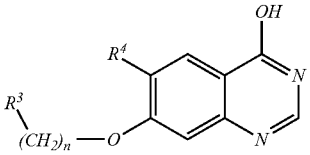

*VII*

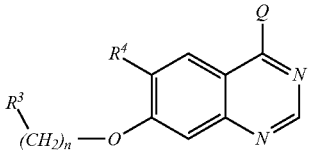

*VIII*

(g) reacting the compound of formula VIII, or its position isomer with an amino group containing compound of the formula IX *or a salt thereof* to replace the leaving group Q and provide a compound of formula X, or its position isomer, as follows:

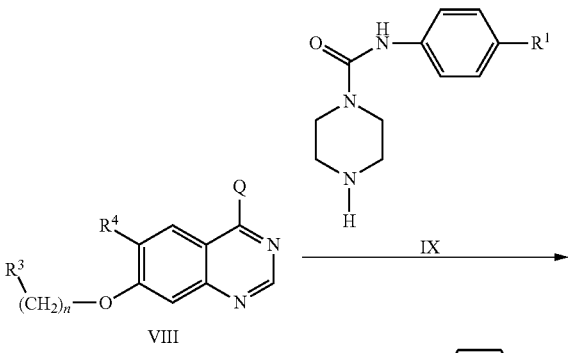

VIII

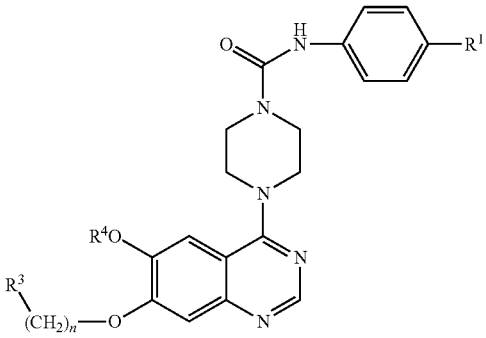

X (h) and optionally, producing a salt, such as the hydrohalide salt, of the compound of formula X, or its position isomer, as follows:

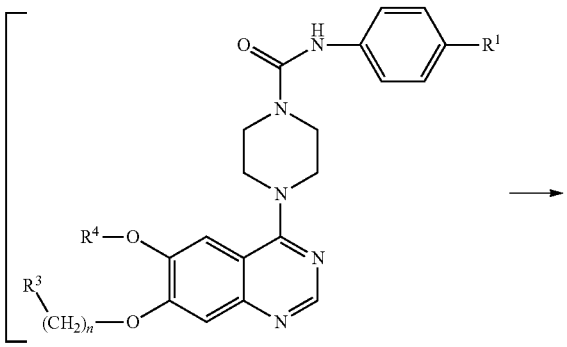

X

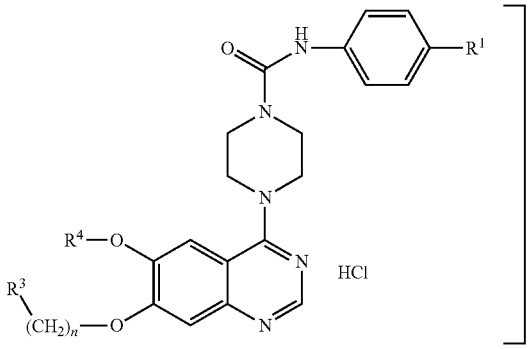

XI

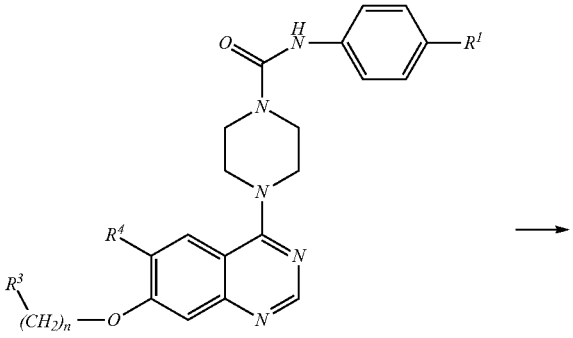

X

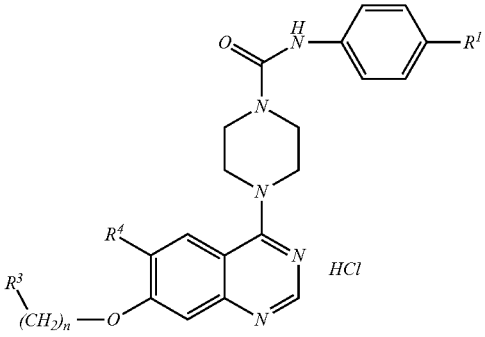

XI and all pharmaceutically acceptable isomers, salts, hydrates, solvates and prodrug derivatives thereof.

The invention also provides a process for preparing an intermediate compound having the formula VIII as follows:

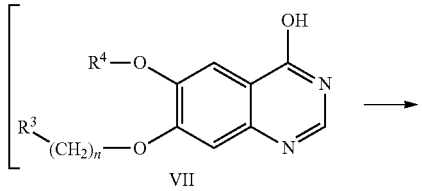

VII

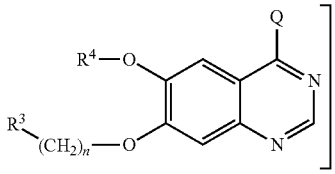

VIII

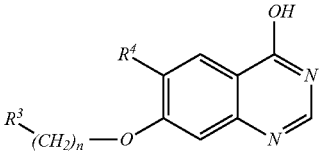

VII

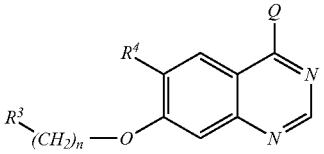

VIII wherein n, $R^3$ and $R^4$ are defined as above, and

Q is a leaving group other than a hydroxyl group, which can be replaced by an amino group or other intermediary group [which is] *to be* subsequently replaced by an amino group, or a salt thereof.

In the above process leaving groups such as halogen, lower alkoxy, lower alkylthio, lower alkylsulfonyloxy, arylsulfonyloxy, etc, may be utilized when necessary except for the reaction point, followed by deprotection. Suitable amino protective groups are, for example, those described in T. W. Greene, Protective Groups in Organic Synthesis, John Wiley & Sons Inc. (1981), etc., such as ethoxycarbonyl, t-butoxycarbonyl, acetyl, benzyl and the like which would be apparent to one of ordinary skill in the art. The protective groups can be introduced and eliminated according to conventional methods used in organic synthetic chemistry, e.g., T. W. Greene, Protective Groups in Organic Synthesis, John Wiley & Sons Inc. (1981).

Appropriate solvents include a lower alcohol, such as methanol, ethanol, isopropanol, etc., a halogenated hydrocarbon, such as chloroform, dichloromethane, etc., an aromatic hydrocarbon, such as benzene, toluene, etc., an ether solvent, such as diethyl ether, THF, 1,4-dioxane, etc., an aprotic polar solvent, such as dimethylformamide, N-methylpyrrolidone, dimethyl sulfoxide, pyridine, etc., or a mixed solvent thereof, optionally in the presence of a base. Examples of the base include organic bases, such as triethylamine, pyridine, etc., inorganic bases, such as potassium carbonate, sodium carbonate, sodium hydroxide, sodium hydride, etc., metal alkoxides, such as sodium methoxide, potassium tert-butoxide, etc., and the like.

In such processes, if the defined groups change under the conditions of the working method or are not appropriate for carrying out the method, the desired compound can be obtained by using the methods for introducing and eliminating protective groups which are conventionally used in organic synthetic chemistry. See, e.g., T. W. Greene, Protective Groups in Organic Synthesis, John Wiley & Sons Inc. (1981), etc. Conversion of functional groups contained in the substituents can be carried out by known methods. See, e.g., R. C. Larock, Comprehensive Organic Transformations (1989), in addition to the above-described processes, and some of the active compounds of formula I may be utilized as intermediates for further synthesizing novel derivatives according to formula A.

The intermediates and the desired compounds in the processes described above can be isolated and purified by purification methods conventionally used in organic synthetic chemistry, for example, neutralization, filtration, extraction, washing, drying, concentration, recrystallization, and various kinds of chromatography. The intermediates may be subjected to the subsequent reaction without purification.

There may be tautomers for some formula A, and the present invention covers all possible isomers including tautomers and mixtures thereof, the process of making would be apparent to one of ordinary skill in the art. Where chiral carbons lend themselves to two different enantiomers, both enantiomers are contemplated as well as procedures for separating the two enantiomers. In the compounds of this invention, carbon atoms bonded to four non-identical substituents are asymmetric. Accordingly, the compounds may also exist as diastereoisomers, enantiomers or mixtures thereof. The syntheses described herein may employ racemates, enantiomers or diastereomers as starting materials or intermediates. Diastereomeric products resulting from such syntheses may be separated by chromatographic or crystallization methods, or by other methods known in the art. Likewise, enantiomeric product mixtures may be separated using the same techniques or by other methods known in the art. Each of the asymmetric carbon atoms, when present in the compounds of this invention, may be in one of two configurations (R or S) and both are within the scope of the present invention. In the processes described above, the final products may, in some cases, contain a small amount of diastereomeric or enantiomeric products, however these products do not affect their therapeutic or diagnostic application.

In the case where a salt of a compound of formula A is desired and the compound is produced in the form of the desired salt, it can be subjected to purification as such. In the case where a compound of formula A is produced in the free state and its salt is desired, the compound of formula A is dissolved or suspended in a suitable organic solvent, followed by addition of an acid or a base to form a salt. Preferably the solvent for the recrystallization and salt formation is a lower alcohol, preferably methanol or ethanol.

The following examples are provided to illustrate the invention. The examples are not intended to limit the scope of the present invention and they should not be so interpreted. Amounts are in weight parts or weight percentages unless otherwise indicated. All of the cited patents and publications are incorporated herein by reference. The following specific examples are provided to better assist the reader in the various aspects of practicing the present invention. As these specific examples are merely illustrative, nothing in the following descriptions should be construed as limiting the invention in any way.

Scheme 1

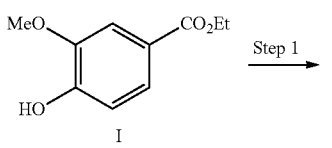

-continued

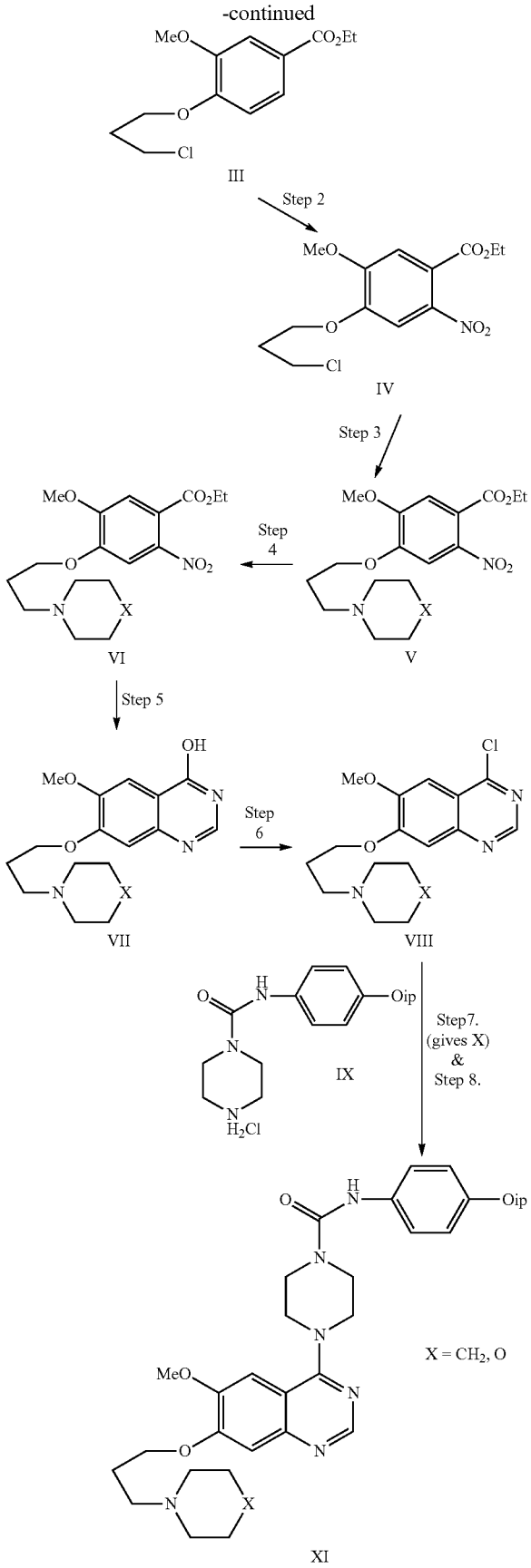

Such examples of the process according to the invention are merely an illustration of a preferred aspect of the invention. Other procedures and adaptations will be apparent to one of ordinary skill in the art upon views these reaction schemes and the structures of the compounds according to the invention. Such procedures are deemed to be within the scope of the present invention.

Also, the compounds of formula A and pharmaceutically acceptable salts thereof may exist in the form of adducts with water (hydrates) or various solvents, which are also within the scope of the present invention.

The following non-limiting examples are provided to better illustrate the present invention.

EXAMPLE 1

Preparation of 4-[6-Methoxy-7-(3-piperidin-1-yl-propoxy)-quinazolin-4-yl]-piperazine-1-carboxylic acid-4-(isopropoxy-phenyl)-amide Step 1

Into a round bottom flask was charged 1-chloro3-bromopropane (1.28 mol) followed by a solution of aqueous potassium carbonate, ethyl vanillate (0.51 mol.) and N-butylammonium bromide (0.0255 mol.) and the resulting reaction mixture was heated to about 70 to about 100° C. for 0.5-4 hours until reaction completion to compound III was confirmed by HPLC/TLC analysis. The reaction mixture was cooled to about 20-25° C. and dichloromethane was added. The resulting biphasic mixture was separated. The organic layer was washed with water then brine solution and the solvent was stripped under vacuum to approximately ⅕ of its original volume. This solution of compound III in dichloromethane was taken on to step #2.

Step 2

Into a round bottom flask equipped with condenser, thermometer and overhead stirrer was charged the solution of III in dichloromethane followed by acetic acid (0.5 L) and the resulting light brown solution was cooled to about 0-5° C. To the rapidly stirring solution was charged dropwise 70% Nitric Acid (1.53 mol.) over about 40-60 minutes. The resulting light brown solution was slowly heated to about 50-70° C. and was allowed to stir at this temperature for about 2-10 hours until reaction completion was confirmed by HPLC/TLC analysis. The orange colored solution was poured into Ice/Water (1.0 L) and dichloromethane (0.5 L). The solution was allowed to warm to about 20° C., the layers were separated and the organic layer was washed several times with de-ionized water followed by brine. The solvent was removed under reduced pressure to approximately ⅕ of the original volume at which time ethanol was introduced. The ethanolic solution was allowed to cool to about 20° C. over 10-16 hours, then further cooled to about 0-10° C. for about 1-3 hours. The off-white solid was collected by vacuum filtration to give about 82% (based on starting weight of I) of IV. Product identity was confirmed by proton NMR, carbon-13 and mass spectral analysis.

Step 3

Into a round bottom flask was charged IV (0.31 mol) followed by toluene (500 ml), an aqueous potassium carbonate solution, N-butylammonium bromide (0.0155 mol), sodium iodide (0.62 mol.) and piperidine (0.93 mol) and the resulting reaction mixture was heated to about 60-100° C. for about 1-10 hours until reaction completion was confirmed by HPLC/TLC analysis. The reaction mixture was cooled to about 20-25° C. and the layers were separated. The aqueous layer was extracted once with toluene. The combined organics were washed with water, 3% thiosulphate solution and then brine. The toluene was removed under reduced pressure to approximately ⅕ of its original volume at which time ethanol (500 ml), and water (200 ml) were added and V was taken in solution into step #4.

Step 4

Into a round bottom flask containing the solution of V in ethanol/water/toluene was charged palladium on carbon catalyst (50% wet) and the reaction mixture was heated to about 40-50° C. To this warmed reaction mixture was charged a pre-made solution of potassium formate (0.62 mol) and formic acid (0.93 mol) in de-ionized water over about 0.5-3 hours maintaining the solution temperature between 40-55° C. and the solution pH between 3-6. The reaction mixture was allowed to stir for about 0.5-4 hours at about 40-50° C. at which time HPLC/TLC analysis confirmed reaction completion. The reaction mixture was filtered through celite. The filtrate was evaporated under atmospheric pressure until a pot temperature of about 80-90° C. was reached. The remaining aqueous solution was cooled to about 20-25° C. at which time ethyl acetate (600 ml) was charged followed by an aqueous potassium carbonate solution sufficient to adjust the pH to >10. After vigorous stirring the layers were separated, the basic aqueous layer was extracted with ethyl acetate and the combined organic layers were washed with water followed by brine solution. This ethyl acetate solution containing VI was taken directly into step #5

Step 5

To a round bottom flask containing VI (0.31 mol) in ethyl acetate and one equipped with mechanical stirrer, thermometer, and distillation apparatus was charged formamide (210 ml) and a distillation of ethyl acetate was commenced until a pot temperature of about 120-130° C. was reached. The reaction mixture was cooled to about 60-80° C. at which time ammonium formate (0.37 mol) was charged. The reaction mixture was further heated to about 110-150° C. for about 2-12 hours, preferably about 130° C. for about six hours, until reaction completion was confirmed by HPLC/TLC analysis. The reaction mixture was cooled to about 20-25° C. at which time diglyme (800 ml) followed by methyl t-butyl ether (260 ml) were charged in succession. The slurry was allowed to stir at about 20-25° C. for about 1-10 hours, preferably 3 hours, and was then cooled to about 0-10° C. for about 1-3 hours. The product was filtered, the cake was washed with MTBE. The wet cake was transferred to another round bottom flask and to the white product was charged MTBE (800 ml) and the slurry was stirred vigorously for about 1-4 hours at about 20-25° C. The product was filtered and washed with MTBE then dried to a constant weight at about 30-50° C. under vacuum to give 70% yield (based on starting weight of IV) of VII. The identity of the product was confirmed by proton, C-13 NMR and mass spectral analysis.

Step 6

Into a round bottom flask equipped with overhead stirrer, thermometer, condenser and nitrogen purge was charged toluene (500 ml) followed by VII (0.28 mol)and the resulting suspension was cooled to about 0-10° C. at which time thionyl chloride (500 ml) was charged in portions over several hours maintaining the solution temperature of at least <25° C. The reaction mixture was re-cooled to about 10-15° C. at which time dimethyl formamide (100 ml) was charged in portions over several hours maintaining the solution temperature of at least <35° C. The reaction mixture was heated to about 80-85° C. where it was maintained for about 1-5 hours until reaction completion was confirmed by HPLC/TLC analysis. To the reaction mixture was charged toluene (500 ml) maintaining the temperature during the addition to at least >50° C. The reaction mixture was allowed to cool to about 20-25° C. and was maintained at this temperature for about 8-16 hours. The resulting precipitated solid was filtered and the cake was washed with toluene. The still toluene wet cake was added in portions to a pre-made solution of 20% potassium bicarbonate and dichloromethane that was cooled to about 0-5° C. After ensuring that a solution pH of at least >10 was obtained, the layers were separated and the aqueous was extracted once more with dichloromethane. The combined organics were washed with water and then brine. The dichloromethane solution was evaporated under reduced pressure at temperature of at least <40° C. to approximately ⅕$^{th}$ of its original volume at which time acetonitrile (1800 ml) was charged. The resulting precipitated white solid was cooled to about 20-25° and was allowed to stir at this temperature for about 4 hours. The product was collected by filtration and washed with acetonitrile to give after drying to a constant weight in vacuo at about 35-50° C., 72% yield of at least >95% VIII. The identity of this product was confirmed by proton, C-13 and mass spectral analysis.

Step 7

Into a round bottom flask equipped with mechanical stirrer, thermometer, reflux condenser and nitrogen purge was charged VIII (0.298 mol), dimethyl formamide (800 ml), potassium carbonate (0.746 mol)) and IX (0.300 mol) and the reaction mixture was stirred at about 20-50° C. for about 2-24 hours, preferably about 6 hours at about 40° C., until reaction completion was confirmed by HPLC/TLC analysis. The reaction mixture was cooled to about 20-25° C. at which time it was charged to a solution of de-ionized water and dichloromethane. The layers were separated and the aqueous layer was extracted with dichloromethane. The organic layers were combined and washed with 20% sodium chloride solution, 20% ammonium chloride solution followed by brine. The dichloromethane (DCM) was removed to approximately ⅕$^{th}$ its original volume by evaporation under reduced pressure at a temperature of at least <40° C. To this DCM solution was charged ethanol (1000 ml) and the solution was heated to about 40-50° C. at which time charcoal was added. The reaction mixture was stirred at about 40-50° C. for about 0.5-1.0 hours and was then filtered over celite to remove charcoal. The filtrate was re-heated to about 40° C. at which time a pre-made solution of sulfuric acid in ethanol was added in portions until a solution pH of about 2-4 was reached. The resulting white slurry was cooled to about 20-25° C. and stirred at this temperature for about 2-8 hours. It was further cooled to about 0-10° C. where it was stirred for about 1-3 hours. The product was collected by filtration and the cake was washed with about 0-10° C. ethanol. The material was dried under vacuum at about 40-50° C. until a constant weight was obtained to give an 80% yield of X with at least >90% purity by HPLC analysis.

Step 8

Into a round bottom flask equipped with mechanical stirrer, condenser, thermometer and argon purge was charged crude X (0.167 mol) followed by ethanol (600 ml) and de-ionized water (200 ml). The reaction mixture was heated to about 55-60° C. at which time total dissolution was achieved. The solution was cooled to about 20-25° C. over at least 1-4 hours, preferably about 3 hours. The reaction mixture was further cooled to about 0-5° C. where it was maintained for about 1-3 hours. The product was collected by filtration, the cake was washed with about 0-5° C. ethanol and was then dried under vacuum at about 35-55° C., preferably about 45° C., until XI with an LOD <1% was obtained. Compound XI was isolated in 83% yield and was found to be at least >99% purity by HPLC analysis with no impurity of at least >0.5%. The identity of this compound was confirmed by comparison to a previously synthesized and filly characterized analytical reference standard.

EXAMPLE 2

Preparation of 4-[6-Methoxy-7-(3-morpholin-4-yl-propoxy)-quinazolin-4-yl]-piperazine-1-carboxylic acid-(4-isopropoxy-phenyl)-amide Step 1

Into a round bottom flask was charged 1-chloro3-bromopropane (1.53 mol) followed by a solution of aqueous potassium carbonate, ethyl vanillate (0.51 mol) and N-butylammonium bromide (0.0255 mol) and the resulting reaction mixture was heated to about 70-100° C. for about 0.5-4 hours until reaction completion to the title compound was confirmed by HPLC/TLC analysis. The reaction mixture was cooled to about 20-25° C. and dichloromethane (500 ml) was added and the resulting biphasic mixture was separated. The organic layer was washed with water then brine solution and the solvent was stripped under vacuum to approximately ⅕ of its original volume. This solution of compound III in dichloromethane was taken on to step #2.

Step 2

Into a round bottom flask equipped with condenser, thermometer and overhead stirrer was charged the solution of III (0.51 mol) in dichloromethane followed by acetic acid (500 ml) and the resulting light brown solution was cooled to about 0-5° C. To the rapidly stirring solution was charged dropwise 70% Nitric Acid (1.53 mol) over about 40-60 minutes. The resulting light brown solution was slowly heated to about 50-70° C. and was allowed to stir at this temperature for about 2-10 hours until reaction completion was confirmed by HPLC/TLC analysis. The red colored solution was poured into Ice/Water (1000 ml) and dichloromethane (500 ml). The solution was allowed to warm to about 20° C., the layers were separated and the organic layer was washed several times with de-ionized water followed by brine. The solvent was removed under reduced pressure to approximately ⅕th of the original volume at which time ethanol was introduced. The solution was allowed to cool to about 20° C. over about 10-16 hours, then further cooled to about 0-10° C. for about 1-3 hours. The off-white solid was collected by vacuum filtration to give 82% (based on starting weight of I) of IV. Product identity was confirmed by proton NMR, carbon-13 and mass spectral analysis.

Step 3

Into a round bottom flask was charged IV (0.315 mol) followed by toluene (500 ml), an aqueous potassium carbonate solution, N-butylammonium bromide (0.0158 mol), sodium iodide (0.48 mol) and morpholine (0.945 mol) and the resulting reaction mixture was heated to about 60-100° C. for about 1-10 hours until reaction completion was confirmed by HPLC/TLC analysis. The reaction mixture was cooled to about 20-25° C. and the layers were separated. The aqueous layer was extracted once with toluene. The combined organics were washed with water, 3% thiosulphate solution and then brine. The toluene was removed under reduced pressure to approximately ⅕$^{th}$ of its original volume at which time ethanol (500 ml), and water (200 ml) were added and V was taken in solution into step #4.

Step 4

Into a round bottom flask containing the solution of V in ethanol/water/toluene was charged palladium on carbon catalyst (50% wet) and the reaction mixture was heated to about 40-50° C. To this warmed reaction mixture was charged a pre-made solution of potassium formate (0.63 mol) and formic acid (0.945 mol) in de-ionized water over about 0.5-3 hours maintaining the solution temperature between 40-55° C. and the solution pH of at least between 3-6. The reaction mixture was allowed to stir for about 0.5-4 hours at about 40-50° C. at which time HPLC/TLC analysis confirmed reaction completion. The reaction mixture was filtered through celite. The filtrate was evaporated under atmospheric pressure until a pot temperature of about 80-90° C. was reached. The remaining aqueous solution was cooled to about 20-25° C. at which time ethyl acetate (500 ml) was charged followed by an aqueous potassium carbonate solution sufficient to adjust the pH to at least >10. After vigorous stirring the layers were separated, the basic aqueous layer was extracted with ethyl acetate and the combined organic layers were washed with water followed by brine solution. This ethyl acetate solution containing VI was taken directly into step #5.

Step 5

To a round bottom flask containing VI (0.315 mol) in ethyl acetate and one equipped with mechanical stirrer, thermometer, and distillation apparatus was charged formamide (210 ml) and a distillation of ethyl acetate was commenced until a pot temperature of about 120-130° C. was reached. The reaction mixture was cooled to about 60-80° C. at which time ammonium formate (0.378 mol) was charged. The reaction mixture was further heated to about 110-150° C. for about 2-12 hours, preferably about 130° C. for about six hours, until reaction completion was confirmed by HPLC/TLC analysis. The reaction mixture was cooled to about 20-25° C. at which time diglyme (800 ml) followed by methyl t-butyl ether (225 ml) were charged in succession. The slurry was allowed to stir at about 20-25° C. for about 1-10 hours, preferably about 3 hours, and was then cooled to about 0-10° C. for about 1-3 hours. The product was filtered, the cake was washed with MTBE. The wet cake was transferred to another round bottom flask and to the white product was charged MTBE (800 ml) and the slurry was stirred vigorously for about 1-4 hours at about 20-25° C. The product was filtered and washed with MTBE then dried to a constant weight at about 30-50° C. under vacuum to give at least 72% yield (based on starting weight of IV) of VII. The identity of the product was confirmed by proton, C-13 NMR and mass spectral analysis.

Step 6

Into a round bottom flask equipped with overhead stirrer, thermometer, condenser and nitrogen purge was charged toluene (500 ml) followed by VII (0.278 mol.)and the resulting suspension was cooled to about 0-10° C. at which time thionyl chloride (500 ml) was charged in portions over several hours maintaining the solution temperature of at least <25° C. The reaction mixture was re-cooled to about 10-15° C. at which time dimethyl formamide (100 ml) was charged in portions over several hours maintaining the solution temperature of at least <35° C. The reaction mixture was heated to about 80-85° C. where it was maintained for about 1-5 hours until reaction completion was confirmed by HPLC/TLC analysis. To the reaction mixture was charged toluene (500 ml) maintaining the temperature during the addition to at least >50° C. The reaction mixture was allowed to cool to about 20-25° C. and was maintained at this temperature for about 8-16 hours. The resulting precipitated solid was filtered and the cake was washed with toluene. The still toluene wet cake was added in portions to a pre-made solution of 20% potassium bicarbonate and dichloromethane that was cooled to about 0-5° C. After ensuring that a solution pH of at least >10 was obtained, the layers were separated and the aqueous was extracted once more with dichloromethane. The combined organics were washed with water and then brine. The dichloromethane solution was evaporated under reduced pressure at temperature of at least <40° C. to approximately $1/5^{th}$ of its original volume at which time acetonitrile (1400 ml) was charged. The resulting precipitated white solid was cooled to about 20-25° and was allowed to stir at this temperature for about 4 hours. The product was collected by filtration and washed with acetonitrile to give after drying to a constant weight in vacuo at about 35-50° C., about 75% yield of at least >95% VIII. The identity of this product was confirmed by proton, C-13 and mass spectral analysis.

Step 7

Into a round bottom flask equipped with mechanical stirrer, thermometer, reflux condenser and nitrogen purge was charged VIII (0.298 mol), dimethyl formamide (800 ml), potassium carbonate (0.745 mol) and IX (0.300 mol) and the reaction mixture was stirred at about 20-50° C. for about 2-24 hours, preferably about 6 hours at about 40° C., until reaction completion was confirmed by HPLC/TLC analysis. The reaction mixture was cooled to about 20-25° C. at which time it was charged to a solution of de-ionized water and dichloromethane. The layers were separated and the aqueous layer was extracted with dichloromethane. The organic layers were combined and washed with 20% sodium chloride solution, 20% ammonium chloride solution followed by brine. The dichloromethane was removed to approximately $1/5^{th}$ its original volume by evaporation under reduced pressure at a temperature of at least <40° C. To this DCM solution was charged ethanol (800 ml) and the solution was heated to about 40-50° C. at which time charcoal was added. The reaction mixture was stirred at about 40-50° C. for about 0.5-1.0 hours and was then filtered over celite to remove charcoal. The filtrate was re-heated to about 40° C. at which time a pre-made solution of sulfuric acid in ethanol was added in portions until a solution pH of at least 2-3 was reached. The resulting white slurry was cooled to about 20-25° C. and stirred at this temperature for about 2-8 hours. It was further cooled to about 0-10° C. where it was stirred for about 1-3 hours. The product was collected by filtration and the cake was washed with about 0-10° C. ethanol. The material was dried under vacuum at about 40-50° C. until a constant weight was obtained to give an 83% yield of X with at least >90% purity by HPLC analysis.

Step 8

Into a round bottom flask equipped with mechanical stirrer, condenser, thermometer and argon purge was charged crude X (0.166 mol) followed by methanol (600 ml) and de-ionized water (40 ml). The reaction mixture was heated to about 50-55° C. at which time total dissolution was achieved. The solution was cooled to about 20-25° C. over about 1-4 hours, preferably about 3 hours. The reaction mixture was further cooled to about 0-5° C. where it was maintained for about 1-3 hours. The product was collected by filtration and the cake was washed with about 0-5° C. methanol and was then dried under vacuum at about 35-55° C., preferably, about 45° C., until XI with an LOD of at least <1% was obtained. Compound XI was isolated in about 75% yield and was found to be at least >99% pure by HPLC analysis with no impurity of at least >0.5%. The identity of this compound was confirmed by comparison to a previously synthesized and fully characterized analytical reference standard.

It is preferred to employ the administration route which is the most effective for the treatment. For example, administration is made orally or non-orally by intrarectal, intraoral, subcutaneous, intramuscular or intravenous administration.

Examples of the forms for administration are capsules, tablets, granules, powders, syrups, emulsions, suppositories and injections.

Liquid compositions such as emulsions and syrups which are appropriate for oral administration can be prepared using water, sugars such as sucrose, sorbitol and fructose, glycols such as polyethylene glycol and propylene glycol, oils such as sesame oil, olive oil and soybean oil, preservatives such as benzoates, flavors such as strawberry flavor and peppermint, etc.

Capsules, tablets, powders and granules can be prepared using excipients such as lactose, glucose, sucrose and mannitol, disintegrating agents such as starch and sodium alginate, lubricants such as magnesium stearate and talc, binders such as polyvinyl alcohol, hydroxypropyl cellulose and gelatin, surfactants such as fatty acid esters, plasticizers such as glycerin, etc.

Compositions for topical application are prepared by dissolving or suspending an active compound in one or more kinds of solvents such as mineral oil, petroleum and polyhydric alcohol, or other bases used for topical drugs.

Compositions for intestinal administration are prepared using ordinary carriers such as cacao fat, hydrogenated fat and hydrogenated fat carboxylic acid, and are provided as suppositories.

Compositions suitable for non-oral administration preferably comprise a sterilized aqueous preparation containing an active compound which is isotonic to the recipient's blood. For example, injections are prepared using a carrier which comprises a salt solution, a glucose solution, or a mixture of a salt solution and a glucose solution. The compositions for non-oral administration may additionally be formulated to contain one or more kinds of additives selected from glycols, oils, flavors, preservatives (including antioxidants), excipients, disintegrating agents, lubricants, binders, surfactants and plasticizers which are used for the preparation of compositions for oral administration.

The effective dose and the administration schedule for each of the compounds of formula (A) or a pharmaceutically acceptable salt thereof will vary depending on the administration route, the patient's age and body weight, and the type or degree of the diseases to be treated. However, it is generally appropriate to administer a compound of formula (A) or a pharmaceutically acceptable salt thereof in a dose of 0.01-1000 mg/adult/day, preferably 5-500 mg/adult/day, in one to several parts.

All the compounds of the present invention produced by the process according to the invention can be immediately applied to the treatment of kinase-dependent diseases of mammals as kinase inhibitors, specifically, those relating to tyrosine kinase. Specifically preferred are the compounds which have IC50 within the range of about 10 nM to about 10 μm. Even more preferred are compounds which have IC50 within the range of about 10 nM to about 1 μM. Most preferred are compounds which have an IC50 value which is smaller than about 1 μM. Specific compounds of the present invention which have an activity to specifically inhibit one of the three types of protein kinase (for example, kinase which phosphorylates tyrosine, kinase which phosphorylates tyrosine and threonine, and kinase which phosphorylates threonine) can be selected. Tyrosine kinase-dependent diseases include hyperproliferative malfunction which is caused or maintained by abnormal tyrosine kinase activity.

Examples include psoriasis, pulmonary fibrosis, glomerulonephritis, cancers, atherosclerosis, and antiangiogenesis (e.g., tumor proliferation or diabetic retinopathy). Although relationships of other classes of kinase to specific diseases are not well known, it is considered that a selective tyrosine kinase-inhibiting compound has a useful therapeutic effect. Also, it is understood that other classes of kinase have their own useful therapeutic effects. Quercetin, genistein and staurosporin which are tyrosine kinase inhibitors inhibit many other protein kinase in addition to the tyrosine kinase, and have strong cytotoxicity as a result of the lack of specificity for them. Accordingly, tyrosine kinase inhibitors (or inhibitors of other kinase) which are apt to induce undesirable side effects due to lack of selectivity can be identified using a usual test for measuring cytotoxicity.

The present invention provides a process for making nitrogen-containing heterocyclic compounds and pharmaceutically acceptable salts thereof which inhibit phosphorylation of PDGF receptor to hinder abnormal cell growth and thus, are useful for the prevention or treatment of cell-proliferative diseases such as arteriosclerosis, vascular reobstruction, cancer and glomerulosclerosis. Other variations on the processes and compounds according to the invention will be apparent upon considering the preferred embodiments of the present invention and are hereby contemplated as being within the scope of the present invention.

Compositions or formulations of the compounds of the invention are prepared for storage or administration by mixing the compound having a desired degree of purity with physiologically acceptable carriers, excipients, stabilizers etc., and may be provided in sustained release or timed release formulations. Acceptable carriers or diluents for therapeutic use are well known in the pharmaceutical field, and are described, for example, in Remington's Pharmaceutical Sciences, Mack Publishing Co., (A. R. Gennaro edit. 1985). Such materials are nontoxic to the recipients at the dosages and concentrations employed, and include buffers such as phosphate, citrate, acetate and other organic acid salts, antioxidants such as ascorbic acid, low molecular weight (less than about ten residues) peptides such as polyarginine, proteins, such as serum albumin, gelatin, or immunoglobulins, hydrophilic polymers such as polyvinylpyrrolidinone, amino acids such as glycine, glutamic acid, aspartic acid, or arginine, monosaccharides, disaccharides, and other carbohydrates including cellulose or its derivatives, glucose, mannose or dextrins, chelating agents such as EDTA, sugar alcohols such as mannitol or sorbitol, counterions such as sodium and/or nonionic surfactants such as TWEEN®, PLURONICS® or polyethyleneglycol.

The term "effective amount" is an amount necessary for administering the compound in accordance with the present invention to provide the necessary effect such as inhibiting the phosphorylation of kinases or treating disease states in a mammal. In accordance with the present invention, a suitable single dose size is a dose that is capable of preventing or treating an animal with a disease when administered one or more times over a suitable time period. Doses can vary depending upon the disease being treated. For example, in the treatment of hypersensitivity, a suitable single dose can be dependent upon the nature of the immunogen causing the hypersensitivity.

An effective administration protocol (i.e., administering a therapeutic composition in an effective manner) comprises suitable dose parameters and modes of administration that result in prevention or treatment of a disease. Effective dose parameters and modes of administration can be determined using methods standard in the art for a particular disease. Such methods include, for example, determination of survival rates, side effects (i.e., toxicity) and progression or regression of disease. For example, the effectiveness of dose parameters and modes of administration of a therapeutic composition of the present invention can be determined by assessing response rates. Such response rates refer to the percentage of treated patients in a population of patients that respond with either partial or complete remission.

Dosage formulations of the compounds of the invention to be used for therapeutic administration must be sterile. Sterility is readily accomplished by filtration through sterile membranes such as 0.2 micron membranes, or by other conventional methods. Formulations typically will be stored in lyophilized form or as an aqueous solution. The pH of the preparations of the invention typically will be about 3-11, more preferably about 5-9 and most preferably about 7-8. It will be understood that use of certain of the foregoing excipients, carriers, or stabilizers will result in the formation of cyclic polypeptide salts. While the preferred route of administration is by injection, other methods of administration are also anticipated such as orally, intravenously (bolus and/or infusion), subcutaneously, intramuscularly, colonically, rectally, nasally, transdermally or intraperitoneally, employing a variety of dosage forms such as suppositories, implanted pellets or small cylinders, aerosols, oral dosage formulations and topical formulations such as ointments, drops and dermal patches. The compounds of the invention are desirably incorporated into shaped articles such as implants which may employ inert materials such as biodegradable polymers or synthetic silicones, for example, Silastic, silicone rubber or other polymers commercially available.

The compounds of the invention may also be administered in the form of liposome delivery systems, such as small unilamellar vesicles, large unilamellar vesicles and multilamellar vesicles. Liposomes can be formed from a variety of lipids, such as cholesterol, stearylamine or phosphatidylcholines.

The compounds of the invention may also be delivered by the use of antibodies, antibody fragments, growth factors, hormones, or other targeting moieties, to which the compound molecules are coupled. The compounds of the invention may also be coupled with suitable polymers as targetable drug carriers. Such polymers can include polyvinylpyrrolidinone, pyran copolymer, polyhydroxypropyl-methacrylamide-phenol, polyhydroxyethyl-aspartamide-phenol, or polyethyleneoxide-polylysine substituted with palmitoyl residues. Furthermore, compounds of the invention may be coupled to a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like.

Therapeutic compound liquid formulations generally are placed into a container having a sterile access port, for example, an intravenous solution bag or vial having a stopper pierceable by hypodermic injection needle.

Therapeutically effective dosages may be determined by either in vitro or in vivo methods. For each particular compound of the present invention, individual determinations may be made to determine the optimal dosage required. The range of therapeutically effective dosages will be influenced by the route of administration, the therapeutic objectives and the condition of the patient. For injection by hypodermic needle, it may be assumed the dosage is delivered into the body's fluids. For other routes of administration, the absorption efficiency must be individually determined for each compound by methods well known in pharmacology. Accordingly, it may be necessary for the therapist to titer the dosage and modify the route of administration as required to obtain the optimal therapeutic effect. The determination of effective dosage levels, that is, the dosage levels necessary to achieve the desired result, will be readily determined by one skilled in the art. Typically, applications of compound are commenced at lower dosage levels, with dosage levels being increased until the desired effect is achieved.

The compounds and compositions of the invention can be administered orally or parenterally in an effective amount within the dosage range of about 0.001 to about 1000 mg/kg, preferably about 0.01 to about 100 mg/kg and more preferably about 0.1 to about 20 mg/kg. Advantageously, the compounds and composition of the invention may be administered several times daily. Other dosage regimens may also be useful (e.g. single daily dose and/or continuous infusion).

Typically, about 0.5 to about 500 mg of a compound or mixture of compounds of the invention, as the free acid or base form or as a pharmaceutically acceptable salt, is compounded with a physiologically acceptable vehicle, carrier, excipient, binder, preservative, stabilizer, dye, flavor etc., as called for by accepted pharmaceutical practice. The amount of active ingredient in these compositions is such that a suitable dosage in the range indicated is obtained.

Typical adjuvants which may be incorporated into tablets, capsules and the like are binders such as acacia, corn starch or gelatin, and excipients such as microcrystalline cellulose, disintegrating agents like corn starch or alginic acid, lubricants such as magnesium stearate, sweetening agents such as sucrose or lactose, or flavoring agents. When a dosage form is a capsule, in addition to the above materials it may also contain liquid carriers such as water, saline, or a fatty oil. Other materials of various types may be used as coatings or as modifiers of the physical form of the dosage unit. Sterile compositions for injection can be formulated according to conventional pharmaceutical practice. For example, dissolution or suspension of the active compound in a vehicle such as an oil or a synthetic fatty vehicle like ethyl oleate, or into a liposome may be desired. Buffers, preservatives, antioxidants and the like can be incorporated according to accepted pharmaceutical practice.

Acid addition salts include hydrochlorides, hydrobromides, hydroiodides, alkylsulphonates, e.g. methanesulphonates, ethanesulphonates, or isethionates, arylsulphonates, e.g. p-toluenesulphonates, besylates or napsylates, phosphates, sulphates, hydrogen sulphates, acetates, trifluoroacetates, propionates, citrates, maleates, fumarates, malonates, succinates, lactates, oxalates, tartrates and benzoates. Salts derived from inorganic or organic bases include alkali metal salts such as sodium or potassium salts, alkaline earth metal salts such as magnesium or calcium salts, and organic amine salts such as morpholine, piperidine, dimethylamine or diethylamine salts. Prodrugs of compounds of formula (1) include those compounds, for example esters, alcohols or aminos, which are convertible in vivo by metabolic means, e.g. by hydrolysis, reduction, oxidation or transesterification, to compounds of formula (1). Particularly useful salts of compounds according to the invention include pharmaceutically acceptable salts, especially acid addition pharmaceutically acceptable salts. Next, the pharmacological activity of the compounds of the present invention are specifically explained by test examples.

The pharmacological activities of the compounds of the present invention are obtained by following the test example procedures as follows, for example.

Biological Test Assay Type 1

Inhibitory Effect on Compounds on Autophosphorylation of Platelet Derived Growth Factor β-PDGF Receptor (1) HR5 Phosphorylation Assay The HR5 cell line is a cell line of CHO cells engineered to overexpress human β-PDGFR, which cell line is available from the ATCC. The expression level of β-PDGFR in HR5 cells is around $5\times10^4$ receptor per cell. For the phosphorylation assay according to the invention, HR5 cells were grown to confluency in 96-well microtiter plates under standard tissue culture conditions, followed by serum-starvation for 16 hours. Quiescent cells were incubated at 37° C. without or with increasing concentrations of the test compound (0.01-30 uM) for 30 minutes followed by the addition of 8 nM PDGF BB for 10 minutes. Cells were lysed in 100 mM Tris, pH7.5, 750 mM NaCl, 0.5% Triton X-100, 10 mM sodium pyrophosphate, 50 mM NaF, 10 ug/ml aprotinin, 10 ug/ml leupeptin, 1 mM phenylmethylsulfonyl fluoride, 1 mM sodium vanadate, and the lysate was cleared by centrifugation at 15,000×g for 5 minutes. Clarified lysates were transferred into a second microtiter plate in which the wells were previously coated with 500 ng/well of 1B5B11 anti-β-PDGFR mAb, and then incubated for two hours at room temperature. After washing three times with binding buffer (0.3% gelatin, 25 mM Hepes pH 7.5, 100 mM NaCl, 0.01% Tween-20), 250 ng/ml of rabbit polyclonal anti-phosphotyrosine antibody (Transduction Laboratory) was added and plates were incubated at 37° C. for 60 minutes. Subsequently, each well was washed three times with binding buffer and incubated with 1 ug/ml of horse radish peroxidase-conjugated anti-rabbit antibody (Boehringer Mannheim) at 37° C. for 60 minutes. Wells were washed prior to adding ABTS (Sigma), and the rate of substrate formation was monitored at 650 nm. The assay results are reported as $IC_{50}$ (expressed as the concentration of a compound according to the invention that inhibits the PDGF receptor phosphorylation by 50%) as compared to control cells that are not exposed to a compound according to the invention.

Examples of such $IC_{50}$ test results in the HR5 assay for compounds according to the invention are set forth below in Table 1.

(1) MG63 Phosphorylation Assay

The MG63 cell line is a human osteosarcoma tumor cell line available from the ATCC. This assay is for measuring endogenous β-PDGFR phosphorylation in MG63 cells. The assay conditions are the same as those described at for HR5 cell, except that PDGF-BB stimulation is provided in the presence or absence of 45% human plasma. The HR5 assay results are reported as an $IC_{50}$ (expressed as the concentration of a compound according to the invention that inhibits the PDGF receptor phosphorylation by 50%) as compared to control cells that are not exposed to a compound according to the invention.

Examples of such $IC_{50}$ test results in the MG63 assay for compounds according to the invention are set forth below in Table 1.

The assay results for Compound Examples [2] *1* and [4] *2* are set forth in Table 1 below.

TABLE 1

| Example Compound | MG63 w/human plasma IC50(μM) | HR5 IC50(μM) |
|---|---|---|
| Example 1 | 0.030 | 0.250 |
| Example 2 | 0.060 | 0.130 |

Biological Test Assay Type 2

Growth Inhibition Against Smooth Muscle Cells

Vascular smooth muscle cells are isolated from a pig aorta by explanation and used for the test. The cells are put into wells of a 96-well plate (8000 cells/well) and cultured in Dulbeccois modified Eagle's medium (DMEM; Nissui Pharmaceutical Co., Ltd.) containing 10% fetal bovine serum (FBS; Hyclone) for 4 days. Then, the cells are further cultured in DMEM containing 0.1% FBS for 3 days, and are synchronized at the cell growth stationary phase.

To each well is added DMEM containing 0.1% FBS and a test sample at a varied concentration, and the cell growth is brought about by PDGF-BB (SIGMA, final concentration: 20 ng/ml). After culturing for 3 days, the cell growth is measured using a cell growth assay kit (Boehringer Mannheim) according to the XTT method [J. Immunol. Methods, 142, 257-265 (1991)], and the cell growth score is calculated by the following equation.

Cell growth score=100×{1-(M-PO)/(P100-PO)} wherein P100=absorbance by XTT reagent when stimulated by PDGF-BB; PO=absorbance by XTT reagent when not stimulated by PDGF-BB, and M=absorbance by XTT reagent after addition of a sample when stimulated by PDGF-BB.

The test result is expressed as the concentration of a test compound which inhibits the cell growth by 50% (IC50).

Biological Test Assay Type 3

Inhibitory Effect on Hypertrophy of Vascular Intima

Male SD rats (weight: 375-445 g, Charles River, golden standard) are anesthetized with sodium pentobarbital (50 mg/kg, i.p.), and then the neck of each animal is incised by the median incision, followed by retrograde insertion of a balloon catheter (2F, Edwards Laboratories) into the left external carotid. After the above treatment is repeated seven times, the catheter is pulled out, the left external carotid is ligated, and the wound is sutured. A test compound is suspended in a 0.5% solution of Tween 80 in an aqueous solution of sodium chloride to a concentration of 20 mg/ml in the case of intraperitoneal administration and in a 0.5% solution of methyl cellulose 400 to a concentration of 6 mg/ml in the case of oral administration. The suspension is administered once a day in the case of intraperitoneal administration and once or twice a day in the case of oral administration for a period of 15 days starting on the day before the balloon injury. On the 14th day after the balloon injury, the animal is killed and its left carotid is extirpated. The tissues are fixed with formalin, wrapped in paraffin and sliced, followed by Elastica Wangeeson staining. The area of the cross section of the vascular tissues (intima and media) is measured with an image analyzer (Luzex F, NIRECO) and the intima/media area ratio (I/M) is regarded as the degree of hypertrophy of the vascular intima.

From the results obtained, it is apparent when the hypertrophy of vascular intima is significantly inhibited by administration of the compounds of the present invention.

Biological Test Assay Type 4

Evaluation by the Use of a Rat Adjuvant Arthritis Model

Dead cells of Mycobacterium bacterium (Difco Laboratories Inc.) are disrupted in agate mortar and suspended in liquid paraffin to the final concentration of 6.6 mg/ml, followed by sterilization with high pressure steam. Then, 100 ml of the suspension is subcutaneously injected into the right hind foot pad of each animal of groups of female 8-weeks-old Lewis rats (Charles River Japan) (6 animals/group) to induce adjuvant arthritis. A test compound is suspended in a 0.5% solution of methyl cellulose to the final concentration of 3 mg/ml, and from just before the induction of arthritis, the suspension is orally administered in an amount of 100 ml/100 g of the body weight once a day, 5 days a week. To a control group is administered a 0.5% solution of methyl cellulose. A normal group is given no adjuvant treatment or test compound administration. The administration of the test compound is continued till the 18th day after the adjuvant treatment. On the 17th day, the number of leukocytes in peripheral blood are counted, and on the 18th day, all the blood is collected, followed by dissection.

The change in body weight with the passage of time, the change of edema in hind foot with the passage of time, the weight of spleen and thymus, the number of leukocytes in peripheral blood, the hydroxyproline content of urine, the glucosaminoglycan content of urine, the SH concentration in serum, the concentration of nitrogen monoxide in serum and the concentration of mucoprotein in serum are measured and evaluated. The volume of each of both hind feet are measured using a rat's hind foot edema measurement device (TK-101, Unicorn). The number of leukocytes in peripheral blood are counted using an automatic multichannel blood cell counter (Sysmex K-2000, Toa Iyo Denshi Co., Ltd.). The hydroxyproline content of urine is measured according to the method described in Ikeda, et al., Annual Report of Tokyo Metropolitan Research Laboratories P. H., 36, 277 (1985), and the glucosaminoglycan content is measured according to the method described in Moriyama, et al., Hinyo Kiyo, 40, 565 (1994) and Klompmakers, et al., Analytical Biochemistry, 153, 80 (1986). The SH concentration in serum is measured according to the method described in Miesel, et al., Inflammation, 17, 595 (1993), and the concentration of nitrogen monoxide is measured according to the method of Tracey, et al., Journal of Pharmacology & Experimental Therapeutics, 272, 1011 (1995). The concentration of mucoprotein is measured using Aspro GP Kit (Otsuka Pharmaceutical Co., Ltd.). The percentage inhibition for each indication is calculated according to the following equation.

% Inhibition={(Control group−Compound-administered group)/(Control group−Normal group)}×100.

From the results obtain from such assays, it is apparent when the compound according to the invention inhibits the occurrence of adjuvant arthritis.

Biological Test Assay Type 5

Activity on a Mesangial Proliferative Glomerulonephritis Model

Anti-rat Thy-1.1 monoclonal antibody OX-7 (Sedaren) is administered to male Wister-Kyoto rats (Charles River Japan, 160 g, 6 animals/group) in an amount of 1.0 mg/kg by intravenous administration through the tail vein. A test compound is suspended in a 0.5% solution of methylcellulose and the resulting suspension is administered to each of the rats twice a day for a period of 7 days starting on the day before the administration of OX-7. On the 7th day after the OX-7 administration, when mesangial cell growth and extracellular matrix hypertrophy become prominent, the left kidney of each rat is extirpated, fixed with 20% buffered formalin for 6 hours and wrapped in paraffin, followed by slicing. The obtained pieces are subjected to immune tissue staining using antibody PC10 (DAKO) against an intranuclear antigen of proliferative cells. After comparative staining with Methyl Green staining solution using diaminobenzidine as a color developer, the paraffin pieces are enclosed. Half of the glomeruli in a kidney piece are observed and the number of the cells in one glomerulus which are positive to the intranuclear antigen of proliferative cells are calculated. The test for the significance of difference is carried out by the Wilcoxon test.

From such results, it is apparent when the compounds according to the present invention show alleviating activity on mesangial proliferative glomerulonephritis.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. The examples given above are non-limiting in that one of ordinary skill in view of the above will readily envision other permutations and variations on the invention without departing from the principal concepts. Such permutations and variations are also within the scope of the present invention. All the patents, journal articles and other documents discussed or cited above are herein incorporated by reference. The invention is further illustrated with reference to the claims that follow thereto.

What is claimed is:

[1. A process for preparing a compound of formula A:

A

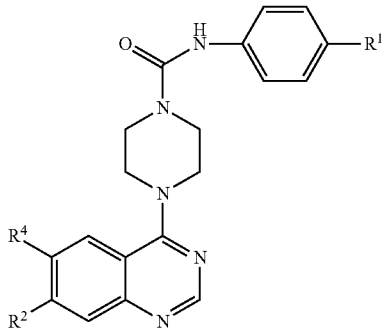

wherein $R^1$ is a member selected from the group consisting of:

—CN, —O-methyl, —O-ethyl, —O-propyl, —O-isopropyl, —O-butyl, —O-t-butyl, —O-isoamyl, 1-naphthyloxy, 2-naphthyloxy, 4-indolyloxy, 5-indolyloxy, 5-isoquinolyloxy;

$R^2$ and $R^4$ are each independently a member selected from the group consisting of:

hydrogen, —O—$CH_3$, —O(—$CH_2$)—$CH_3$, —O(—$CH_2$)$_2$—$CH_3$, —O—$CH_2$—CH═$CH_2$, —O—$CH_2$—C═CH and —O(—$CH_2$)$_n$—$R^3$; wherein one of the $R^2$ and $R^4$ groups is —O(—$CH_2$)$_n$—$R^3$ and the remaining $R^2$ or $R^4$ group is other than —O(—$CH_2$)$_n$—$R^3$;

n is 2 to 5;

$R^3$ is a member selected from the group consisting of:

piperidine, pyrrolidine, morpholine, piperazine, 4-methylpiperidine and 2-methyl-piperidine, and all pharmaceutically acceptable isomers, salts, hydrates, solvates and N-acylated derivatives thereof, comprising the steps of:

(a) etherifying the hydroxy group of a compound of formula I or its position isomer with a compound of formula II wherein $L_1$ is a leaving group, under basic etherification conditions in the presence of an appropriate solvent to produce a compound of formula III or its position isomer as follows:

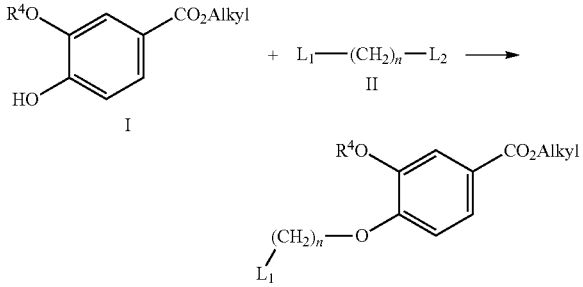

(b) nitrating the compound according to formula III, or its position isomer, to yield a compound according to formula IV, or its position isomer, at a suitable temperature in a solvent as follows:

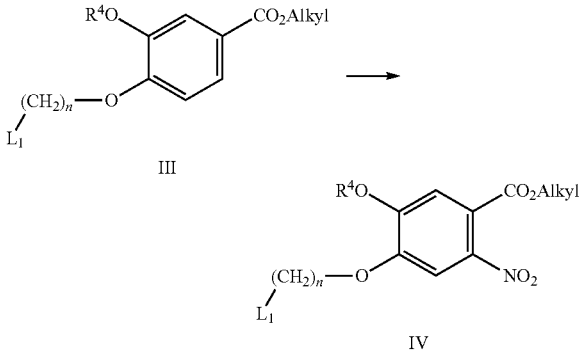

(c) reacting the compound of formula IV, or its position isomer, with an amine containing compound selected from the group consisting of piperidine, pyrrolidine, morpholine, piperazine, 4-methyl-piperidine and 2-methyl-piperidine, in the presence of a catalyst and a solvent to provide a compound of formula V, or its position isomer, as follows:

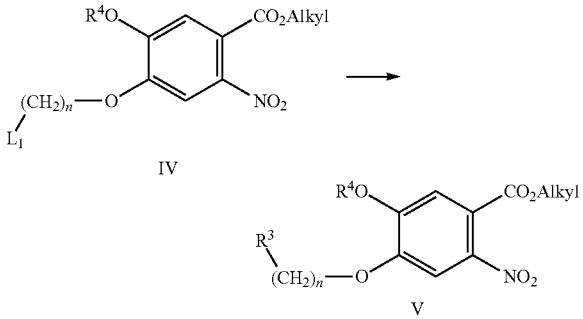

(d) reducing the nitro group on the compound of formula V, or on its position isomer, to an amino group and thereby producing a compound of formula VI, or its position isomer, as follows:

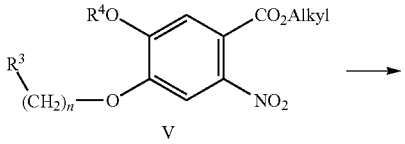

-continued

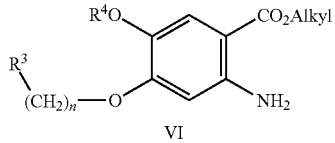

(e) reacting the compound of formula VI, or its position isomer with ammonium formate and formamide at a suitable temperature to produce a cyclized quinazoline derivative of formula VII, or its position isomer, as follows:

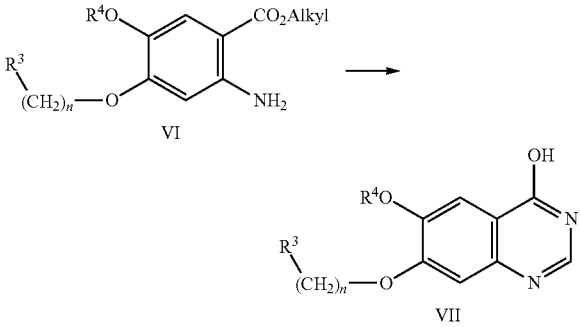

(f) replacing the hydroxy group of the compound of formula VII, or its position isomer, with a leaving group Q to provide a compound of formula VIII, or its position isomer, as follows:

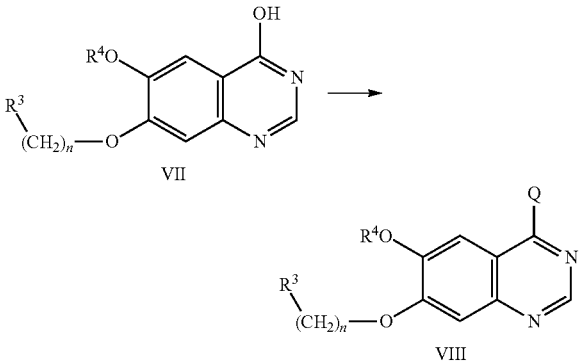

(g) reacting the compound of formula VIII, or its position isomer, with a compound of the formula IX, or a salt thereof, to provide a compound of formula X, or its position isomer, as follows:

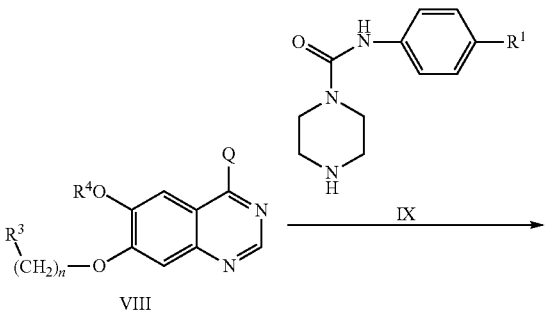

-continued

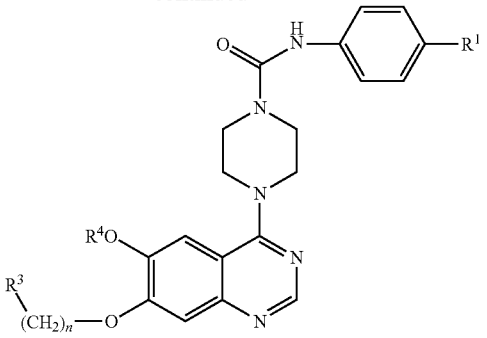

X (h) and optionally, producing a salt, solvate, hydrate, or N-acylated, of the compound of formula X, or its position isomer.]

[2. The process according to claim 1 wherein the leaving group $L_1$ in step (a) is selected from the group consisting of Cl, Br, p-toluenesulfonate and methyl sulfonate.]

[3. The process according to claim 1 wherein the leaving group $L_2$ in step (a) is selected from the group consisting of Cl, Br, p-toluenesulfonate and methyl sulfonate.]

[4. The process according to claim 1 wherein the solvent in step (a) is selected from the group consisting of toluene, methanol, ethanol, ether, and THF.]

[5. The process according to claim 1 wherein the base in step (a) is selected from the group consisting of potassium carbonate, sodium carbonate, and sodium hydroxide.]

[6. The process according to claim 1 wherein step (a) is conducted for about 2 to about 6 hours.]

[7. The process according to claim 1 wherein the compound in step (b) is nitrated at a temperature of from about 0 to about 80° C.]

[8. The process according to claim 1 wherein the catalyst in step (c) is selected from the group consisting of potassium carbonate, sodium carbonate, sodium hydroxide, and sodium iodide.]

[9. The process according to claim 1 wherein the solvent in step (c) is selected from the group consisting of toluene, ethanol, ether, THF, glyme, diglyme, and MTBE.]

[10. The process according to claim 1 wherein cyclization step (e) is conducted at a temperature of about 100° C. to about 200° C.]

[11. The process according to claim 1 wherein the leaving group Q is selected from the group consisting of Cl, Br, p-toluene sulfonate and methyl sulfonate.]

[12. The process according to claim 1 wherein $R^3$ in compound of Formula A is a member selected from the group consisting of piperidine, pyrrolidine, morpholine, piperazine, 4-methyl-piperidine and 2-methyl-piperidine and all pharmaceutically acceptable isomers, salts, hydrates, solvates and N-acylated derivatives thereof.]

[13. The process according to claim 12 wherein $R^1$ is a member selected from the group consisting of CN and —O-isopropyl, n is 2 or 3, and $R^3$ is selected from the group consisting of piperidine, pyrrolidine, morpholine, piperazine, 4-methyl-piperidine and 2-methyl-piperidine, and position isomers and homologues thereof, and all pharmaceutically acceptable isomers, salts, hydrates, solvates and N-acylated derivatives thereof.]

[14. The process according to claim 12, wherein $R^1$ is a member selected from the group consisting of CN and —O-isopropyl, n is 2 or 3, and $R^3$ is a substituted or unsubstituted piperidinyl or pyrrolidinyl radical, and position isomers and homologues thereof, and all pharmaceutically acceptable isomers, salts, hydrates, solvates and N-acylated derivatives thereof.]

[15. The process according to claim 1 which is a process for making a compound according to formula A(1) or formula A(2):

Formula A(1)

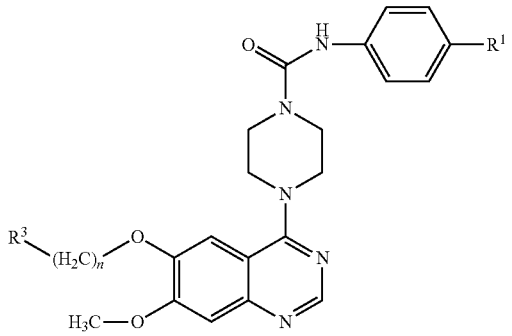

Formula A(2)

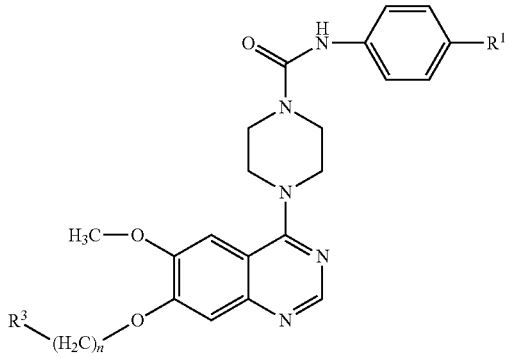

wherein $R^1$ is a member selected from the group consisting of:

—CN, —O-methyl, —O-ethyl, —O-propyl, —O-isopropyl, —O-butyl, —O-t-butyl, —O-isoamyl, 1-naphthyloxy, 2-naphthyloxy, 4-indolyloxy, 5-indolyloxy, 5-isoquinolyloxy; and all pharmaceutically acceptable isomers, salts, hydrates, solvates and N-acylated derivatives thereof.]

[16. The process according to claim 15, wherein $R^1$ is —O-isopropyl or CN, n is 2 or 3, and $R^3$ is selected from the group consisting of piperidine, pyrrolidine, morpholine, piperazine, 4-methyl-piperidine and 2-methyl-piperidine, and all pharmaceutically acceptable isomers, salts, hydrates, solvates and N-acylated derivatives thereof.]

[17. The process according to claim 15, wherein n is 3, $R^1$ is —O-isopropyl or CN and $R^3$ is a member selected from the group consisting of;

piperidine, pyrrolidine, morpholine, piperazine, 4-methyl-piperidine and 2-methyl-piperidine and all pharmaceutically acceptable isomers, salts, hydrates, solvates and N-acylated derivatives thereof.]

[18. The process according to claim 15, wherein n is 3, $R^1$ is —O-isopropyl or CN and $R^3$ is selected from the group consisting of piperidine, pyrrolidine, morpholine, piperazine, 4-methyl-piperidine and 2-methyl-piperidine and all pharmaceutically acceptable isomers, salts, hydrates, solvates and N-acylated derivatives thereof.]

[19. The process according to claim 18, wherein n is 3, $R^1$ is —O-isopropyl or CN and $R^3$ is N-piperidine or N-pyrrolidine, and all pharmaceutically acceptable isomers, salts, hydrates, solvates and N-acylated derivatives thereof.]

[20. A process for preparing an intermediate compound having formula VIII, comprising the step of replacing the hydroxy group of the compound of formula VII, or its position isomer, with a leaving group Q to provide a compound of formula VIII, or its position isomer, as follows:

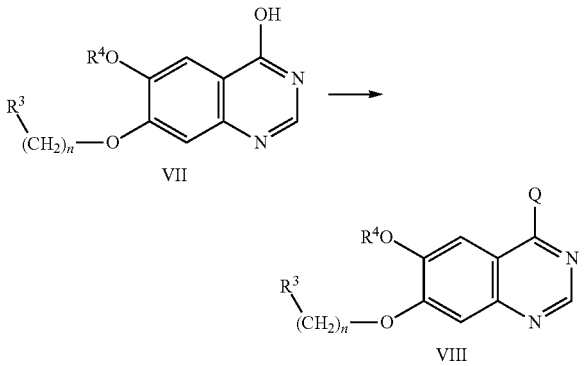

wherein n, $R^3$ and $R^4$ are defined as in claim 1, and

Q is a leaving group other than a hydroxyl group, which can be replaced by an amino group or other intermediary group which is subsequently replaced by an amino group, or a salt thereof.]

[21. A process for preparing a compound of formula A:

A

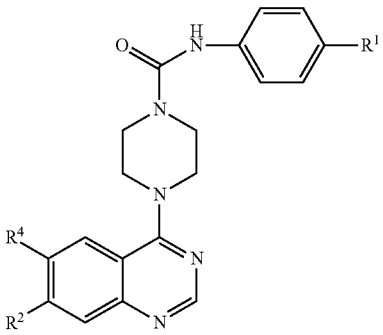

wherein $R^1$ is a member selected from the group consisting of: —CN, —O-methyl, —O-ethyl, —O-propyl, —O-isopropyl, —O-butyl, —O-t-butyl, —O-isoamyl, 1-naphthyloxy, 2-naphthyloxy, 4-indolyloxy, 5-indolyloxy, 5-isoquinolyloxy;

$R^2$ and $R^4$ are each independently a member selected from the group consisting of: hydrogen, —O—$CH_3$, —O(—$CH_2$)—$CH_3$, —O(—$CH_2$)$_2$—$CH_3$, —O—$CH_2$—CH=$CH_2$, —O—$CH_2$—C=CH and —O(—$CH_2$)$_n$—$R^3$; wherein one of the $R^2$ and $R^4$ groups is —O(—$CH_2$)$_n$—$R^3$ and the remaining $R^2$ or $R^4$ group is other than —O(—$CH_2$)$_n$—$R^3$;

n is 2 to 5;

$R^3$ is a member selected from the group consisting of: piperidine, pyrrolidine, morpholine, piperazine, 4-methyl-piperidine and 2-methyl-piperidine, and all pharmaceutically acceptable isomers, salts, hydrates, solvates and N-acylated derivatives thereof, comprising:

etherifying the hydroxy group of a compound of formula I or its position isomer with a compound of formula II wherein $L_1$ is a leaving group, under basic etherification conditions in the presence of an appropriate solvent to produce a compound of formula III or its position isomer as follows:]

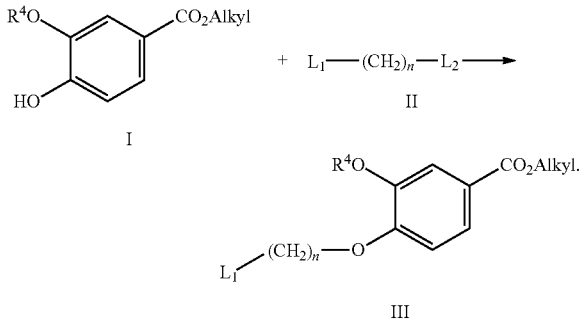

[22. A process for preparing a compound of formula A:

A

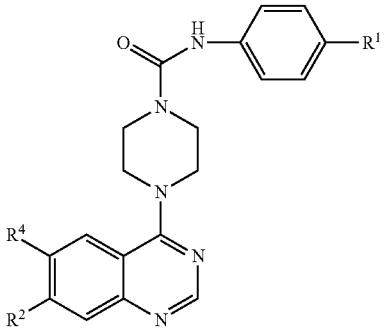

wherein $R^1$ is a member selected from the group consisting of: —CN, —O-methyl, —O-ethyl, —O-propyl, —O-isopropyl, —O-butyl, —O-t-butyl, —O-isoamyl, 1-naphthyloxy, 2-naphthyloxy, 4-indolyloxy, 5-indolyloxy, 5-isoquinolyloxy;

$R^2$ and $R^4$ are each independently a member selected from the group consisting of: hydrogen, —O-$CH_3$, —O(—$CH_2$)—$CH_3$, —O(—$CH_2$)$_2$—$CH_3$, —O—$CH_2$—CH=$CH_2$, —O—$CH_2$—C=CH and —O(—$CH_2$)$_n$ —$R^3$; wherein one of the $R^2$ and $R^4$ groups is —O(—$CH_2$)$_n$ —$R^3$ and the remaining $R^2$ or $R^4$ group is other than —O(—$CH_2$)$_n$—$R^3$;

n is 2 to 5;

$R^3$ is a member selected from the group consisting of: piperidine, pyrrolidine, morpholine, piperazine, 4-methyl-piperidine and 2-methyl-piperidine, and all pharmaceutically acceptable isomers, salts, hydrates, solvates and N-acylated derivatives thereof, comprising:

nitrating the compound according to formula III, or its position isomer, to yield a compound according to formula IV, or its position isomer, at a suitable temperature in solvent as follows: ]

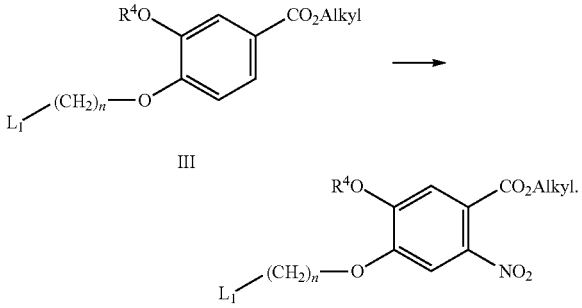

III

IV

[23. A process for preparing a compound of formula A:

A

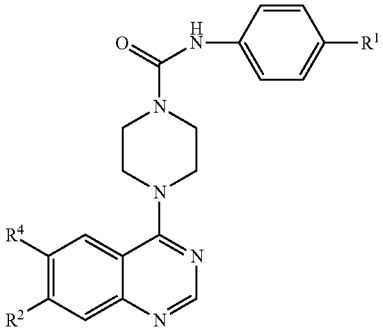

wherein $R^1$ is a member selected from the group consisting of:

—CN, —O-methyl, —O-ethyl, —O-propyl, —O-isopropyl, —O-butyl, —O-t-butyl, —O-isoamyl, 1-naphthyloxy, 2-naphthyloxy, 4-indolyloxy, 5-indolyloxy, 5-isoquinolyloxy;

$R^2$ and $R^4$ are each independently a member selected from the group consisting of:

hydrogen, —O—$CH_3$, —O(—$CH_2$)—$CH_3$, —O(—$CH_2$)$_2$—$CH_3$, —O—$CH_2$—CH═$CH_2$, —O—$CH_2$—C═CH and —O(—$CH_2$)$_n$—$R^3$; wherein one of the $R^2$ and $R^4$ groups is —O(—$CH_2$)$_n$—$R^3$ and the remaining $R^2$ or $R^4$ group is other than —O(—$CH_2$)$_n$—$R^3$;

n is 2 to 5;

$R^3$ is a member selected from the group consisting of:

piperidine, pyrrolidine, morpholine, piperazine, 4-methyl-piperidine and 2-methyl-piperidine, and all pharmaceutically acceptable isomers, salts, hydrates, solvates and N-acylated derivatives thereof, comprising:

reacting the compound of formula IV, or its position isomer, with an amine containing compound selected from the group consisting of piperidine, pyrrolidine, morpholine, piperazine, 4-methyl-piperidine and 2-methyl-piperidine for the appropriate $R^3$ group, in the presence of a basic catalyst and a solvent to replace the $L_1$ group with an $R^3$ group, and provide a compound of formula V, or its position isomer, as follows:]

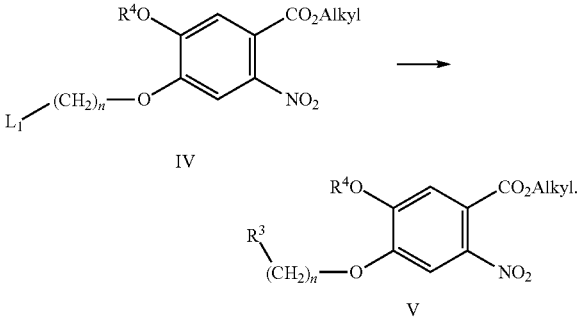

IV

V

[24. A process for preparing a compound of formula A:

A

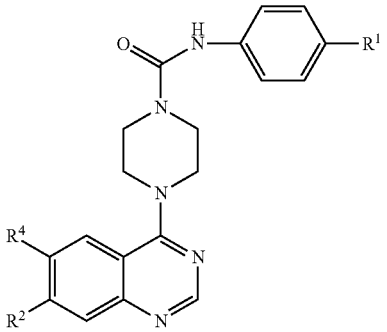

wherein $R^1$ is a member selected from the group consisting of:

—CN, —O-methyl, —O-ethyl, —O-propyl, —O-isopropyl, —O-butyl, —O-t-butyl, —O-isoamyl, 1-naphthyloxy, 2-naphthyloxy, 4-indolyloxy, 5-indolyloxy, 5-isoquinolyloxy;

$R^2$ and $R^4$ are each independently a member selected from the group consisting of:

hydrogen, —O—$CH_3$, —O(—$CH_2$)—$CH_3$, —O(—$CH_2$)$_2$—$CH_3$, —O—CH2—CH═$CH_2$, —O—$CH_2$C═CH and —O(—$CH_2$)$_n$—$R^3$; wherein one of the $R^2$ and $R^4$ groups is —O(—$CH_2$)$_n$—$R^3$ and the remaining $R^2$ or $R^4$ group is other than —O(—$CH_2$)$_n$—$R^3$;

n is 2 to 5;

$R^3$ is a member selected from the group consisting of:

piperidine, pyrrolidine, morpholine, piperazine, 4-methyl-piperidine and 2-methyl-piperidine, and all pharmaceutically acceptable isomers, salts, hydrates, solvates and N-acylated derivatives thereof, comprising:

reducing the nitro group on the compound of formula V, or on its position isomer, to an amino group and thereby producing a compound of formula VI, or its position isomer, as follows:]

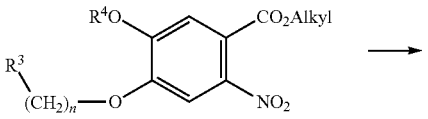

V

-continued

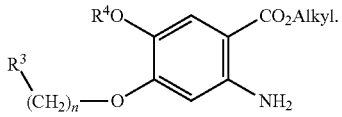

VI

[25. A process for preparing a compound of formula A:

A

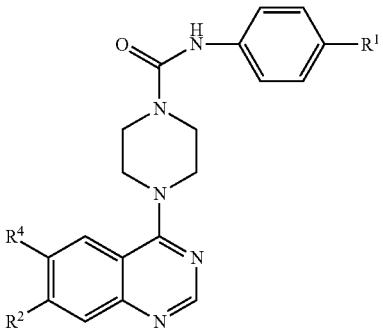

wherein $R^1$ is a member selected from the group consisting of:

—CN, —O-methyl, —O-ethyl, —O-propyl, —O-isopropyl, —O-butyl, —O-t-butyl, —O-isoamyl, 1-naphthyloxy, 2-naphthyloxy, 4-indolyloxy, 5-indolyloxy 5-isoquinolyloxy;

$R^2$ and $R^4$ are each independently a member selected from the group consisting of:

hydrogen, —O—$CH_3$, —O(—$CH_2$)—$CH_3$, —O(—$CH_2$)$_2$—$CH_3$, —O—$CH_2$—CH═$CH_2$, —O—$CH_2$—C═CH and —O(—$CH_2$)$_n$—$R^3$; wherein one of the $R^2$ and $R^4$ groups is —O(—$CH_2$)$_n$—$R^3$ and the remaining $R^2$ or $R^4$ group is other than —O(—$CH_2$)$_n$—$R^3$;

n is 2 to 5;

$R^3$ a member selected from the group consisting of:

piperidine, pyrrolidine, morpholine, piperazine, 4-methylpiperidine and 2-methyl-piperidine, and all pharmaceutically acceptable isomers, salts, hydrates, solvates and N-acylated derivatives thereof, comprising:

reacting the compound of formula VI, or its position isomer with ammonium formate and formamide at a suitable temperature to produce a cyclized quinazoline derivative of formula VII, or its position isomer, as follows:]

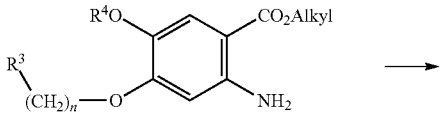

VI

-continued

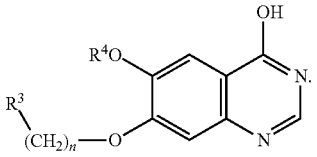

VII

[26. A process for preparing a compound of formula A:

A

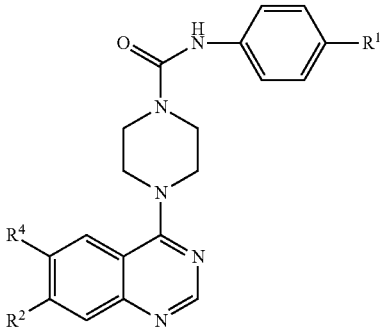

wherein $R^1$ is a member selected from the group consisting of:

—CN, —O-methyl, —O-ethyl, —O-propyl, —O-isopropyl, —O-butyl, —O-t-butyl, —O-isoamyl, 1-naphthyloxy, 2-naphthyloxy, 4-indolyloxy, 5-indolyloxy, 5-isoquinolyloxy $R^2$ and $R^4$ are each independently a member selected from the group consisting of:

hydrogen, —O—$CH_3$, —O(—$CH_2$)—$CH_3$, —O(—$CH_2$)$_2$—$CH_3$, —O—$CH_2$—CH═$CH_2$, —O—$CH_2$—C═CH and —O(—$CH_2$)$_n$—$R^3$; wherein one of the $R^2$ and $R^4$ groups is —O(—$CH_2$)$_n$—$R^3$ and the remaining $R^2$ or group is other than —O(—$CH_2$)$_n$—$R^3$;

n is 2 to 5;

$R^3$ is a member selected from the group consisting of:

piperidine, pyrrolidine, morpholine, piperazine, 4-methylpiperidine and 2-methyl-piperidine, and all pharmaceutically acceptable isomers, salts, hydrates, solvates and N-acylated derivatives thereof, comprising:

replacing the hydroxy group of the compound of formula VII, or its position isomer, with a leaving group Q to provide a compound of formula VIII, or its position isomer, as follows:]

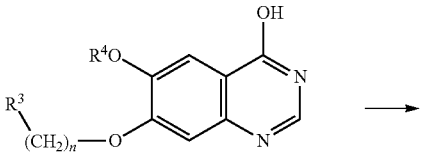

VII

-continued

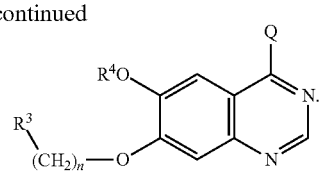

VIII

[27. A process for preparing a compound of formula A:

A

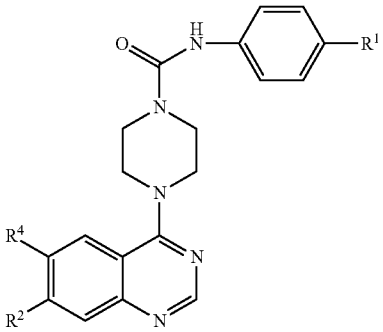

wherein $R^1$ is a member selected from the group consisting of:

—CN, —O-methyl, —O-ethyl, —O-propyl, —O-isopropyl, —O-butyl, —O-t-butyl, —O-isoamyl, 1-naphthyloxy, 2-naphthyloxy, 4-indolyloxy, 5-indolyloxy, 5-isoquinolyloxy $R^2$ and $R^4$ are each independently a member selected from the group consisting of:

hydrogen, —O—$CH_3$, —O(—$CH_2$)—$CH_3$, —O(—$CH_2$)$_2$—$CH_3$, —O—$CH_2$—CH═$CH_2$, —O—$CH_2$—C═CH and —O(—$CH_2$)$_n$—$R^3$; wherein one of the $R^2$ and $R^4$ groups is —O(—$CH_2$)$_n$—$R^3$ and the remaining $R^2$ or $R^4$ group is other than —O(—$CH_2$)$_n$—$R^3$;

n is 2 to 5;

$R^3$ is a member selected from the group consisting of:

piperidine, pyrrolidine, morpholine, piperazine 4-methyl-piperidine and 2-methyl-piperidine, and all pharmaceutically acceptable isomers, salts, hydrates, solvates and N-acylated derivatives thereof, comprising:

reacting the compound of formula VIII, or its position isomer, with a compound of the formula IX, or a salt thereof, to provide a compound of formula X, or its position isomer, as follows:]

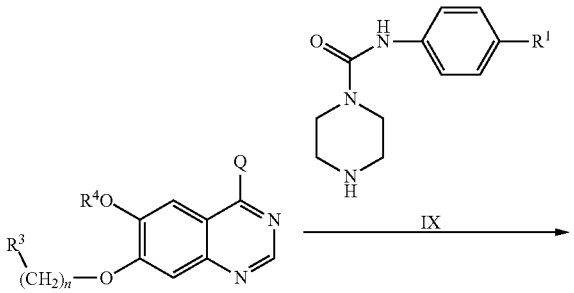

VIII

-continued

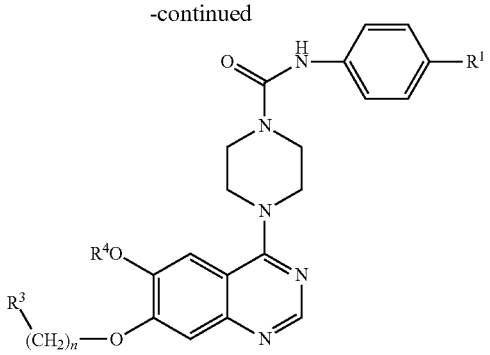

X

[28. The process of claim 27 further comprising producing a salt, solvate, hydrate or prodrug of the compound of formula X.]

[29. The process of claim 28 further comprising producing a salt, hydrate, or combination thereof of the compound of formula X.]

[30. The process according to claim 27 which is a process for making a compound according to formula A(1) or formula A(2):

Formula A(1)

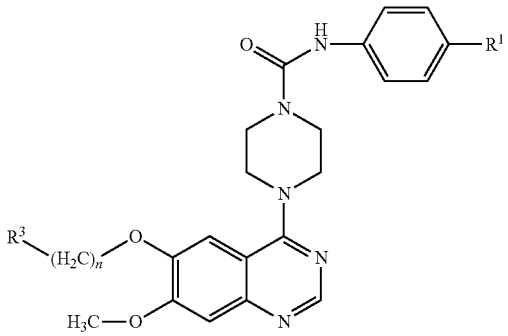

Formula A(2)

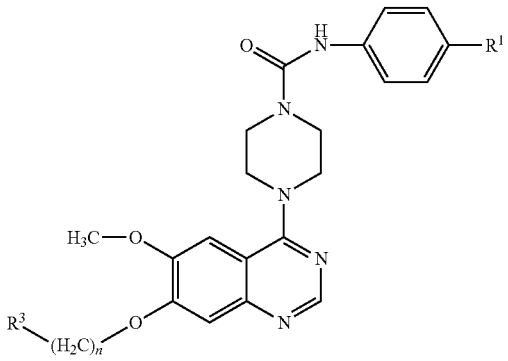

wherein $R^1$ is a member selected from the group consisting of:

—CN, —O-methyl, —O-ethyl, —O-propyl, —O-isopropyl, —O-butyl, —O-t-butyl, —O-isoamyl, 1-naphthyloxy, 2-naphthyloxy, 4-indolyloxy, 5-indolyloxy, 5-isoquinolyloxy;

and all pharmaceutically acceptable isomers, salts, hydrates, solvates and N-acylated derivatives thereof.]

[31. The process according to claim 30, wherein $R^1$ is —O-isopropyl or CN, n is 2 or 3, and $R^3$ is a member selected from the group consisting of piperidine, pyrrolidine, morpholine, piperazine, 4-methyl-piperidine and 2-methyl-piperidine, as well as position isomers and homologues thereof, and all pharmaceutically acceptable isomers, salts, hydrates, solvates and N-acylated derivatives thereof.]

[32. The process according to claim 30, wherein n is 3, $R^1$ is —O-isopropyl or CN and $R^3$ a member selected from the group consisting of:

piperidine, pyrrolidine, morpholine, piperazine, 4-methyl-piperidine and 2-methyl-piperidine and all pharmaceutically acceptable isomers, salts, hydrates, solvates and N-acylated derivatives thereof.]

[33. The process according to claim 30, wherein n is 2, $R^1$ is —O-isopropyl or CN and $R^3$ is selected from the group consisting of:

piperidine, pyrrolidine, morpholine, piperazine, 4-methyl-piperidine and 2-methyl-piperidine and all pharmaceutically acceptable isomers, salts, hydrates, solvates and N-acylated derivatives thereof.]

[34. The process according to claim 18, wherein n is 3, $R^1$ is —O-isopropyl or CN and $R^3$ is N-piperidine or N-morpholine, and all pharmaceutically acceptable isomers, salts, hydrates, solvates and N-acylated derivatives thereof.]

*35. A process for preparing a compound of formula X:*

X

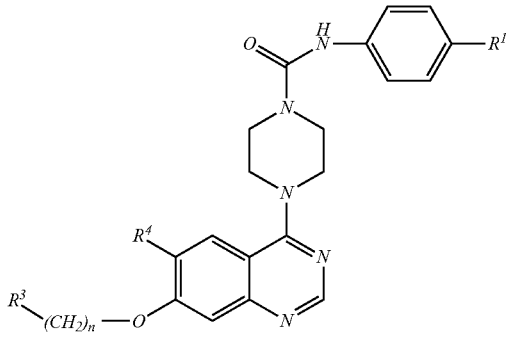

*and all pharmaceutically acceptable salts and hydrates thereof wherein $R^1$ is a member selected from the group consisting of: —CN, —O-methyl, —O-ethyl, —O-propyl, —O-isopropyl, —O-butyl, —O-t-butyl, —O-isoamyl, 1-naphthyloxy, 2-naphthyloxy, 4-indolyloxy, 5-indoylyoxy, 5-isoquinolyloxy; $R^4$ is selected from the group consisting of: hydrogen, —O-$CH_3$, —O(—$CH_2$) —$CH_3$, —O(—$CH_2$)$_2$ —$CH_3$, —O—$CH_2$—CH═$CH_2$, —O—$CH_2$—C≡CH; n is 2 to 5; $R^3$ is a member selected from the group consisting of: piperidine, pyrrolidine, morpholine, piperazine, 4-methyl-piperidine and 2-methyl-piperidine, and all pharmaceutically acceptable salts and hydrates thereof, comprising the steps of: (a) etherifying the hydroxy group of a compound of formula I with a compound of formula II, under basic etherification conditions in the presence of an appropriate solvent to produce a compound of formula III as follows:*

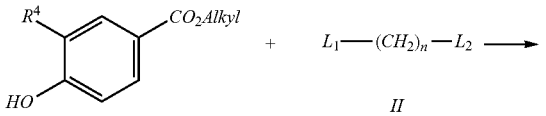

I II

-continued

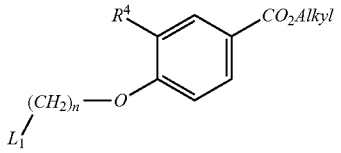

III

*(b) nitrating the compound according to formula III to yield a compound according to formula IV at a suitable temperature in a solvent as follows:*

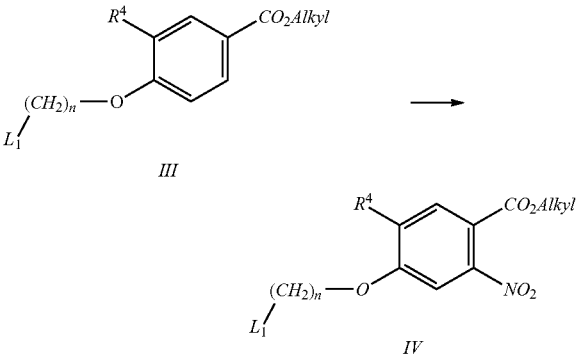

III IV

*(c) reacting the compound of formula IV with an amine containing compound selected from the group consisting of piperidine, pyrrolidine, morpholine, piperazine, 4-methyl-piperidine and 2-methyl-piperidine, in the presence of a catalyst and a solvent to provide a compound of formula V as follows:*

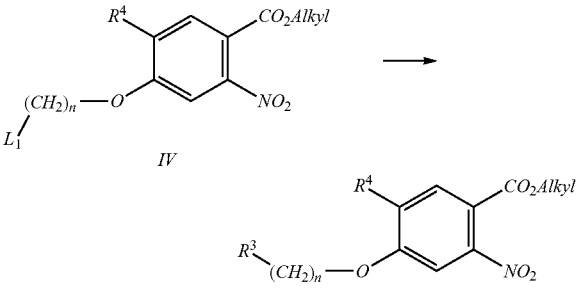

IV V

*(d) reducing the nitro group on the compound of formula V to an amino group and thereby producing a compound of formula VI as follows:*

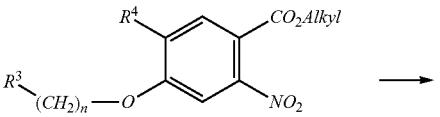

V

-continued

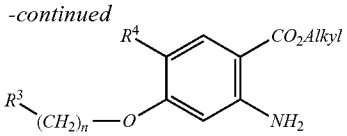

VI (e) reacting the compound of formula VI with ammonium formate and formamide at a suitable temperature to produce a cyclized quinazoline derivative of formula VII as follows:

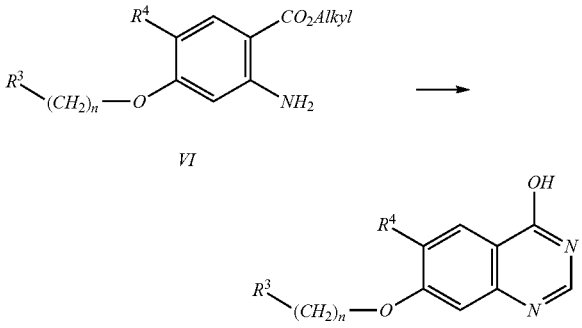

VI

VII (f) replacing the hydroxy group of the compound of formula VII with a leaving group Q to provide a compound of formula VIII as follows:

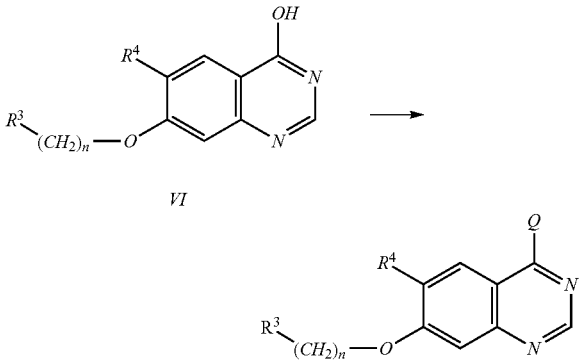

VI

VIII (g) reacting the compound of formula VIII with a compound of the formula IX, or a salt thereof, to provide a compound of formula X as follows:

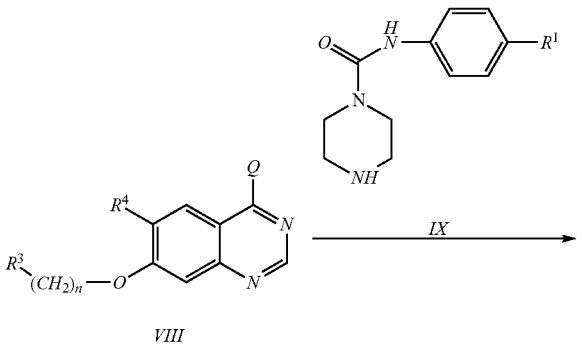

VIII

-continued

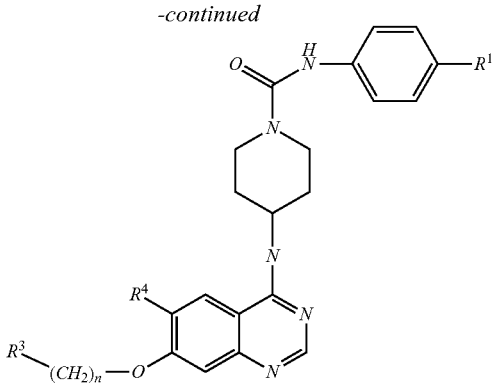

X (h) and optionally, producing a salt or hydrate of the compound of formula X and each $L_1$, $L_2$ or Q is a leaving group, independently selected from the group consisting of halogen, alkoxy, aryloxy, alkylthio, alkylsulfinyl, alkylsulfonyl, alkylsulfonyloxy and arylsulfonyloxy.

36. A process for preparing a compound of formula X:

X

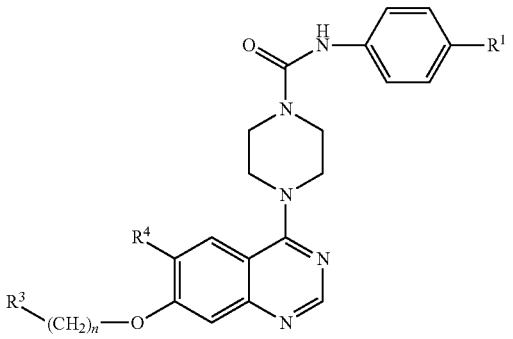

and all pharmaceutically acceptable salts and hydrates thereof, wherein $R^1$ is a member selected from the group consisting of: —CN, —O-methyl, —O-ethyl, —O-propyl, —O-isopropyl, —O-butyl, —O-t-butyl, —O-isoamyl, 1-naphthyloxy, 2-naphthyloxy, 4-indolyloxy, 5-indolyloxy, 5-isoquinolyloxy; $R^4$ is a member selected from the group consisting of: hydrogen, —O—$CH_3$, —O(—$CH_2$)—$CH_3$, —O(—$CH_2$)$_2$—$CH_3$, —O—$CH_2$—CH═$CH_2$, —O—$CH_2$—C≡CH and —O(—$CH_2$)$_n$—$R^3$; n is 2 to 5; $R^3$ is a member selected from the group consisting of: piperidine, pyrrolidine, morpholine, piperazine, 4-methyl-piperidine and 2-methyl-piperidine, comprising at least one of: (a) etherifying the hydroxy group of a compound of formula I with a compound of formula II, under basic etherification conditions in the presence of an appropriate solvent to produce a compound of formula III as follows:

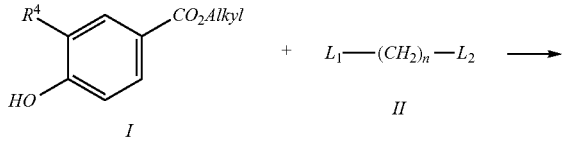

I

II

-continued

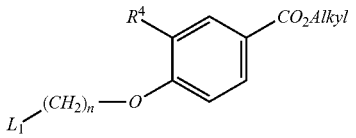

III (b) nitrating the compound according to formula III to yield a compound according to formula IV at a suitable temperature in a solvent as follows:

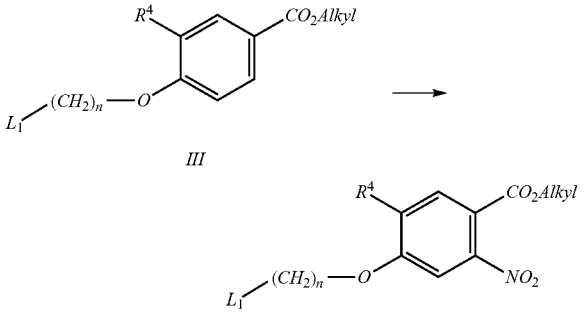

IV (c) reacting the compound of formula IV with an amine containing compound selected from the group consisting of piperidine, pyrrolidine, morpholine, piperazine, 4-methyl-piperidine and 2-methyl-piperidine, in the presence of a catalyst and a solvent to provide a compound of formula V as follows:

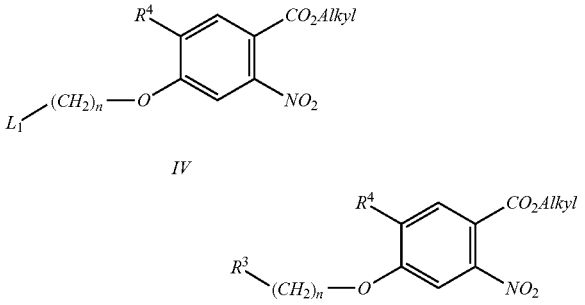

V (d) reducing the nitro group on the compound of formula V to an amino group and thereby producing a compound of formula VI as follows:

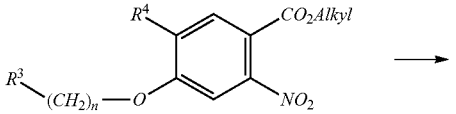

V

-continued

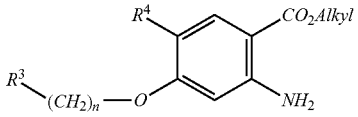

VI (e) reacting the compound of formula VI with ammonium formate and formamide at a suitable temperature to produce a cyclized quinazoline derivative of formula VII as follows:

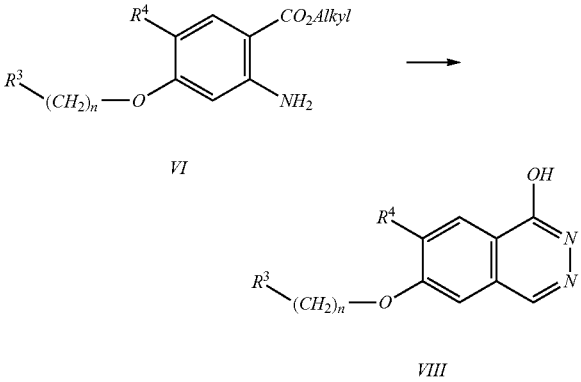

VIII (f) replacing the hydroxy group of the compound of formula VII with a leaving group Q to provide a compound of formula VIII as follows:

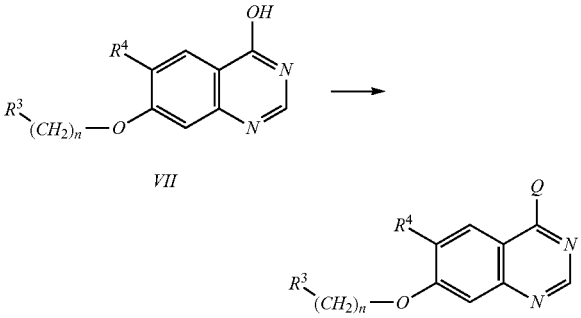

VIII and further converting the product of said step(s) to a compound of formula X or (g) reacting the compound of formula VIII with a compound of the formula IX, or a salt thereof, to provide a compound of formula X as follows:

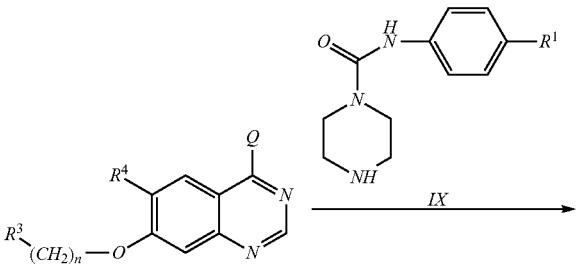

VIII

-continued

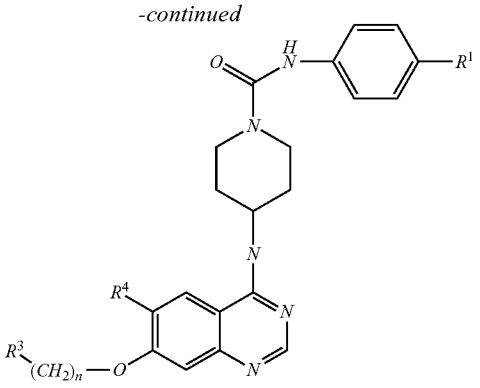

X wherein each of $L_1$, $L_2$ or Q is independently selected from the group consisting of halogen, alkoxy, aryloxy, alkylthio, alkylsulfinyl, alkylsulfonyl, alkylsulfonyloxy and arylsulfonyloxy.

37. The process of claim 36, wherein $R^4$ is —O—$CH_3$.

38. The process of claim 36, wherein $R^1$ is —O-isopropyl or —CN.

39. The process of claim 36, wherein n is 3 and $R^3$ is N-piperidine, N-pyrrolidine or morpholine.

40. The process according to claim 36, wherein each leaving group $L_1$, $L_2$ or Q is independently selected from the group consisting of Cl, Br, p-toluenesulfonyloxy and methyl sulfonyloxy.

41. The process according to claim 36, wherein the solvent in step (a) is selected from the group consisting of toluene, methanol, ethanol, ether, and THF.

42. The process according to claim 36, wherein the base in step (a) is selected from the group consisting of potassium carbonate, sodium carbonate, and sodium hydroxide.

43. The process according to claim 36, wherein step (a) is conducted for about 2 to about 6 hours.

44. The process according to claim 36, wherein the compound in step (b) is nitrated at a temperature of from about 0° C. to about 80° C.

45. The process according to claim 36, wherein the catalyst in step (c) is selected from the group consisting of potassium carbonate, sodium carbonate, sodium hydroxide, and sodium iodide.

46. The process according to claim 36, wherein the solvent in step (c) is selected from the group consisting of toluene, ethanol, ether, THF, glyme, diglyme, and MTBE.

47. The process according to claim 36, wherein cyclization step (e) is conducted at a temperature of about 100° C. to about 200° C.

48. The process according to claim 36, wherein $R^1$ is selected from the group consisting of —CN and —O-isopropyl and n is 2 or 3.

49. The process according to claim 36, wherein $R^1$ is selected from the group consisting of —CN and —O-isopropyl, n is 2 or 3, and $R^3$ is piperidine or pyrrolidine.

50. The process according to claim 36, wherein n is 2 and $R^1$ is —O-isopropyl or –CN.

51. The process according to claim 36, wherein $R^4$ is —O—$CH_3$, n is 3 and $R^1$ is —O-isopropyl or —CN.

52. The process according to claim 51, wherein $R^3$ is

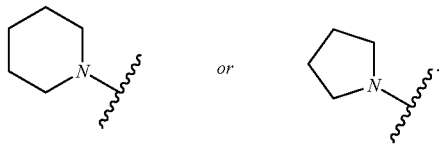

53. The process of claim 36 further comprising producing a salt or hydrate of the compound of formula X.

54. The process of claim 36 further comprising producing a salt, hydrate, or combination thereof of the compound of formula X.

* * * * *